United States Patent
Bhatia et al.

(10) Patent No.: US 11,556,579 B1
(45) Date of Patent: Jan. 17, 2023

(54) SERVICE ARCHITECTURE FOR ONTOLOGY LINKING OF UNSTRUCTURED TEXT

(71) Applicant: Amazon Technologies, Inc., Seattle, WA (US)

(72) Inventors: Parminder Bhatia, Seattle, WA (US); Thiruvarul Selvan Senthivel, Snoqualmie, WA (US); Emine Busra Celikkaya, Seattle, WA (US); Jeremy Douglas Fehr, Seattle, WA (US); Arjun Mukhopadhyay, Seattle, WA (US); Shyam Ramaswamy, Seattle, WA (US); Arun Kumar Ravi, Kirkland, WA (US)

(73) Assignee: Amazon Technologies, Inc., Seattle, WA (US)

( * ) Notice: Subject to any disclaimer, the term of this patent is extended or adjusted under 35 U.S.C. 154(b) by 436 days.

(21) Appl. No.: 16/714,243

(22) Filed: Dec. 13, 2019

(51) Int. Cl.
 *G06F 16/36* (2019.01)
 *G06F 16/33* (2019.01)
 (Continued)

(52) U.S. Cl.
 CPC ........ *G06F 16/367* (2019.01); *G06F 16/3346* (2019.01); *G06N 20/00* (2019.01); *G16H 50/20* (2018.01)

(58) Field of Classification Search
 CPC .. G06F 16/367; G06F 16/3346; G06F 16/313; G06F 16/358; G06F 16/355;
 (Continued)

(56) References Cited

U.S. PATENT DOCUMENTS 9,996,670 B2   6/2018  Dejori
10,607,042 B1  3/2020  Dasgupta et al.
(Continued)

OTHER PUBLICATIONS

Bhatia et al., "Comprehend Medical: a Named Entity Recognition and Relationship Extraction Web Service", arXiv:1910.07419v1, Oct. 15, 2019, 8 pages.
(Continued)

*Primary Examiner* — Shahid A Alam
(74) *Attorney, Agent, or Firm* — Nicholson De Vos Webster & Elliott LLP

(57) ABSTRACT

Techniques for ontology linking of unstructured text as a service are described. A service may receive a request to link unstructured text to a standardized ontology, and the service may segment and tokenize the unstructured text and send the result to multiple services implementing multiple deep machine learning models trained to identify particular entities and one or more relationships between entities. The service may perform a search of the standardized ontology to identify a set of similar candidates from the standardized ontology for the detected entities and the one or more relationships, and then rank the set of similar candidates from the standardized ontology according to their similarity to the detected entities within the unstructured text. The output from the service may include a result identifying a highest ranked candidate of the set of similar candidates from the standardized ontology for the detected entities within the unstructured text.

20 Claims, 17 Drawing Sheets

(51) Int. Cl.
*G16H 50/20* (2018.01)
*G06N 20/00* (2019.01)

(58) Field of Classification Search
CPC .... G06F 16/9024; G06F 16/285; G06F 16/93;
G06F 16/951; G06F 16/958
USPC .......................................... 707/736; 706/12
See application file for complete search history.

(56) References Cited

U.S. PATENT DOCUMENTS

| | | | |
|---|---|---|---|
| 10,740,561 | B1 | 8/2020 | Cao et al. |
| 10,770,180 | B1 | 9/2020 | Kemp et al. |
| 2011/0246462 | A1 | 10/2011 | Wu et al. |
| 2012/0215559 | A1 | 8/2012 | Flanagan et al. |
| 2012/0278102 | A1 | 11/2012 | Johnson |
| 2015/0324454 | A1 | 11/2015 | Roberts et al. |
| 2016/0048655 | A1 | 2/2016 | Maitra et al. |
| 2016/0140210 | A1 | 5/2016 | Pendyala et al. |
| 2016/0148116 | A1* | 5/2016 | Bornea ............... G06F 16/337 706/12 |
| 2017/0075904 | A1 | 3/2017 | Hedges |
| 2017/0372220 | A1 | 12/2017 | Krishnamurthy et al. |
| 2018/0075012 | A1 | 3/2018 | Allen et al. |
| 2018/0082183 | A1 | 3/2018 | Hertz et al. |
| 2018/0089383 | A1 | 3/2018 | Allen et al. |
| 2018/0293227 | A1 | 10/2018 | Guo |
| 2019/0163875 | A1 | 5/2019 | Allen et al. |
| 2019/0354544 | A1* | 11/2019 | Hertz .................. G06F 16/338 |
| 2020/0090033 | A1 | 3/2020 | Ramachandran et al. |
| 2020/0134422 | A1 | 4/2020 | Gliozzo et al. |
| 2020/0210867 | A1 | 7/2020 | Banis et al. |
| 2020/0218744 | A1 | 7/2020 | Wang et al. |
| 2021/0081717 | A1 | 3/2021 | Creed et al. |
| 2021/0200951 | A1 | 7/2021 | Gao et al. |

OTHER PUBLICATIONS

CMS.gov, "ICD-10", Centers for Medicare & Medicaid Services, Available Online at <https://www.cms.gov/Medicare/Coding/ICD10?redirect=/ICD10>, Oct. 1, 2015, pp. 1-2.

CMS.gov, "ICD-10-CM Official Guidelines for Coding and Reporting", Available Online at <http://www.cms.gov/Medicare/Coding/ICD10/downloads/7_Guidelines10cm2010.pdf>, 2010, pp. 1-98.

Devlin et al., "BERT: Pre-training of Deep Bidirectional Transformers for Language Understanding", arXiv:1810.04805v2, May 24, 2019, 16 pages.

U.S. National Library of Medicine, "RxNorm", Available Online at <https://www.nlm.nih.gov/research/umls/rxnorm/index.html>, Unified Medical Language System (UMLS), U.S. Department of Health & Human Services, Dec. 16, 2019, 1 page.

U.S. National Library of Medicine, "Unified Medical Language System (UMLS)", U.S. Department of Helath & Human Services, Available Online at <https://www.nlm.nih.gov/research/umls/index.html>, May 23, 2019, pp. 1-2.

Jagannatha et al, "Structured prediction models for RNN based sequence labeling in clinical text", 2016, In Proceedings of the conference on empirical methods in natural language processing, conference on empirical methods in natural language processing Nov. 2016 (vol. 2016, p. 856). NIH Public Access.

Magge et al, "Clinical NER and relation extraction using bi-char-LSTMs and random forest classifiers", May 2018, In International Workshop on Medication and Adverse Drug Event Detection May 16, 2018 (pp. 25-30). PMLR.

Mandya et al, "Combining long short term memory and convolutional neural network for cross-sentence n-ary relation extraction:, Nov. 2018, arXiv preprint arXiv:1811.00845. Nov. 2018, pp. 1-9.

Non-Final Office Action, U.S. Appl. No. 16/437,338, dated Dec. 6, 2021, 21 pages.

Vaswani et al, "Attention is all you need", 2017, In Advances in neural information processing systems 2017 (pp. 5998-6008).

Verga et al, "Attending to all mention pairs for full abstract biological relation extraction", Oct. 2017, arXiv preprint arXiv:1710.08312. Oct. 23, 2017.

Zheng et al, "Joint entity and relation extraction based on a hybrid neural network", 2017, In Neurocomputing. Sep. 27, 2017; 257:59-66.

Bhatia et al, "End-to-end joint entity extraction and negation detection for clinical text", Jan. 2019, In International Workshop on Health Intelligence, Jan. 27, 2019 (pp. 139-148). Springer, Cham.

Bhatia et al, "Joint entity extraction and assertion detection for clinical text", Dec. 2018, arXiv preprint arXiv: 1812.05270. Dec. 13, 2018, pp. 1-6.

Liang et al, "A novel approach towards medical entity recognition in Chinese clinical text", Jul. 2017, Journal of Healthcare Engineering. Jul. 5, 2017; 201, pp. 1-17.

Liu et al, "AZDrugMiner: an information extraction system for mining patient-reported adverse drug events in online patient forums", 2013, In International conference on smart health Aug. 3, 2013 (pp. 134-150). Springer, Berlin, Heidelberg.

Notice of Allowance, U.S. Appl. No. 16/437,338, dated Jun. 30, 2022, 12 pages.

Rumeng et al., "A hybrid neural network model for joint prediction of presence and period assertions of medical events in clinical notes", 2017, In AMIA Annual Symposium Proceedings 2017 (vol. 2017, p. 1149-1158). American Medical Informatics Association.

Notice of Allowance, U.S. Appl. No. 16/437,338, dated Aug. 29, 2022, 3 pages.

Notice of Allowance, U.S. Appl. No. 16/437,338, dated Oct. 4, 2022, 3 pages.

* cited by examiner

```
{
    "ENTITIES": [
        {
            "ID": 1,
            "BEGINOFFSET": 7,
            "ENDOFFSET": 22,
            "SCORE": 0.9998517036437988,
            "TEXT": "SODIUM CHLORIDE",
            "CATEGORY": "MEDICATION",
            "TYPE": "GENERIC_NAME",
            "TRAITS": [],
            "ATTRIBUTES": [
                {
                    "TYPE": "ROUTE_OR_MODE",
                    "SCORE": 0.32359644770622253,
                    "RELATIONSHIPSCORE": 0.9719992280006409,
                    "ID": 0,
                    "BEGINOFFSET": 0,
                    "ENDOFFSET": 6,
                    "TEXT": "INFUSE",
                    "TRAITS": []
                },
...
                {
                    "TYPE": "DURATION",
                    "SCORE": 0.9392423033714294,
                    "RELATIONSHIPSCORE": 0.9961885809898376,
                    "ID": 8,
                    "BEGINOFFSET": 91,
                    "ENDOFFSET": 97,
                    "TEXT": "3 DAYS",
                    "TRAITS": []
                }
            ]
        }
    ],
    "UNMAPPEDATTRIBUTES": [
        {
            "TYPE": "MEDICATION",
            "ATTRIBUTE": {
                "TYPE": "DOSAGE",
                "SCORE": 0.9922149777412415,
                "ID": 4,
                "BEGINOFFSET": 37,
                "ENDOFFSET": 44,
                "TEXT": "1000 ML",
                "TRAITS": []
            }
        },
        {
            "TYPE": "MEDICATION",
            "ATTRIBUTE": {
                "TYPE": "RATE",
                "SCORE": 0.9728594422340393,
                "ID": 7,
                "BEGINOFFSET": 72,
                "ENDOFFSET": 81,
                "TEXT": "200 ML/HR",
                "TRAITS": []
            }
        }
    ]
}
```

(ABBREVIATED) RESULT 300

*FIG. 3*

▼ Results (8)

| Entity | | Type | Score | Matched concept | Traits |
|---|---|---|---|---|---|
| ☐ fluoride | | Generic name | 0.8024 | Sodium Fluoride 0.011 MG/MG Oral Gel<br>0.9764 score<br>1486566 concept code | -- |
| | topical<br>0.9994 relationship score | Route or mode | 0.8542 | -- | -- |
| | 1.1 %<br>0.989 relationship score | Strength | 0.9982 | -- | -- |
| | topical gel<br>0.9993 relationship score | Form | 0.9336 | -- | -- |

Results (2)

🔍 Find concepts/entities fluoride

Top inferred concepts

| | | |
|---|---|---|
| 1486566 | Sodium Fluoride 0.011 MG/MG Oral Gel | 0.9764 score |
| 347669 | Sodium Fluoride 0.0123 MG/MG Oral Gel | 0.8594 score |
| 1546240 | Sodium Fluoride 0.011 MG/MG Oral Gel [FluoriSHIELD] | 0.8418 score |
| 1297381 | Hydrofluoric Acid 0.01 MG/MG Phosphoric acid 0.012 MG/MG / Sodium Fluoride 0.018 MG/MG Oral Gel | 0.7141 score |
| 701932 | Stannous Fluoride 0.014 MG/MG Oral Gel | 0.4964 score |

▲ More information fluoride

Top inferred concepts

| | | |
|---|---|---|
| 1310123 | Fluorine | 0.9384 score |
| 9873 | Sodium Fluoride | 0.9175 score |
| 1435860 | magnesium fluoride | 0.8125 score |
| 236 | Acidulated Phosphate Fluoride | 0.4175 score |
| 328162 | Sodium Fluoride 0.55 MG Oral Tablet | 0.3522 score |

▲ More information

< 1 >

410
412
414

500 → API call:

```
1  {
2      "Text" : "fluoride topical ( fluoride 1.1% topical
           gel ) 1 application Topically daily Brush onto
3          teeth before bed time , spit , do not rinse ,
           eat or drink for 20-30 minutes"
   }
```

FIG. 5A

502 → API response:

```
1   {
2       "ConceptName" : "Sodium Fluoride 0      ⎫
            .011 MG/MG Oral Gel",                ⎬ 504
3       "ConceptId" : "1486566",                 ⎪
4       "Score" : 0.9764410257339478            ⎭
5   },
6   {
7       "ConceptName" : "Sodium Fluoride 0      ⎫
            .011 MG/MG Oral Gel                  ⎪
            [FluoriSHIELD] ",                    ⎬ 506
8       "ConceptId" : "1546240",                 ⎪
9       "Score" : 0.8418328762054443            ⎭
10  },
11  {
12      "ConceptName" : "Hydrofluoric Acid      ⎫
            0.01 MG/MG / Phosphoric acid 0       ⎪
            0.112 MG/MG / Sodium Fluoride        ⎬ 508
            0.018 MG/MG / Oral Gel ",            ⎪
13      "ConceptId" : "1297381",                 ⎪
14      "Score" : 0.7141376733779907            ⎭
15  },
```

FIG. 5B

SERVICE ARCHITECTURE FOR ONTOLOGY LINKING OF UNSTRUCTURED TEXT

BACKGROUND

As the amount of data generated and utilized in modern computing continues to expand, a relatively new problem has arisen regarding how to effectively manage and utilize the sheer volume of data. As one example, many organizations have large amounts of unstructured alphanumeric data including textual notes or summaries. While such data is easily utilized and understood by human readers, it is incredibly difficult if not impossible for computing applications to be able to use data in this format, which may be disorganized or organized according to different people's preferences, include different word spellings or acronyms across different users, include varying amounts of detail, etc.

For example, business intelligence type applications are typically designed to provide specific analytics, and thus require a specific data schema or arrangement of data to operate upon. Thus, these applications are not able to utilize the various types of data provided by unstructured data, as unstructured data cannot provide any explicit data structure and instead may or may not provide dimensions or identification attributes, such as tags or metadata that may describe the unstructured data. Further, in the rare case that some business's unstructured data conforms to an explicit structure, it typically will not be compatible with existing business applications. As unstructured data typically does not provide a schema or other data descriptor that may be interpreted by current applications, these applications will fail to extract any base data on which analytics can be run. Finally, as unstructured data is often in different formats and structures—even within a same service area, market, type and/or content—current applications are thus unable to make assumptions about data. As a result, attempts to automate the use of current business intelligence systems on various unstructured data sources have failed.

Some methods have been developed to attempt to bring unstructured data into existing business intelligence type applications, such as via manual tagging. However, manually tagging unstructured data by human taggers to provide a well-defined structure is completely impractical in most systems having large amounts of data, and furthermore manual processes typically produce significant numbers of errors. Thus, manual tagging fails to scale as the amount of unstructured data grows, resulting in a significant number of errors being introduced into the data. Further, although some attempts have been made to create automated tagging software, these systems similarly tend to introduce many errors and typically only work for specific use cases.

BRIEF DESCRIPTION OF DRAWINGS

Various embodiments in accordance with the present disclosure will be described with reference to the drawings, in which:

FIG. 3 is a diagram illustrating an example result including detected entities and relationships according to some embodiments.

FIG. 4B is a diagram illustrating an exemplary graphical user interface of results of the request in FIG. 4A for presenting the detected entities and a matched concept from the medical ontology according to some embodiments.

FIG. 4C is a diagram illustrating another exemplary graphical user interface of results of the request in FIG. 4A for presenting matched concepts for detected entities from the medical ontology according to some embodiments.

FIG. 5A is a diagram illustrating an exemplary API call for inputting unstructured text for a request to link the input text with a medical ontology according to some embodiments.

FIG. 5B is a diagram illustrating an exemplary API response of results of the request in FIG. 5A for presenting the matched concepts from the medical ontology according to some embodiments.

DETAILED DESCRIPTION

Figure 1:
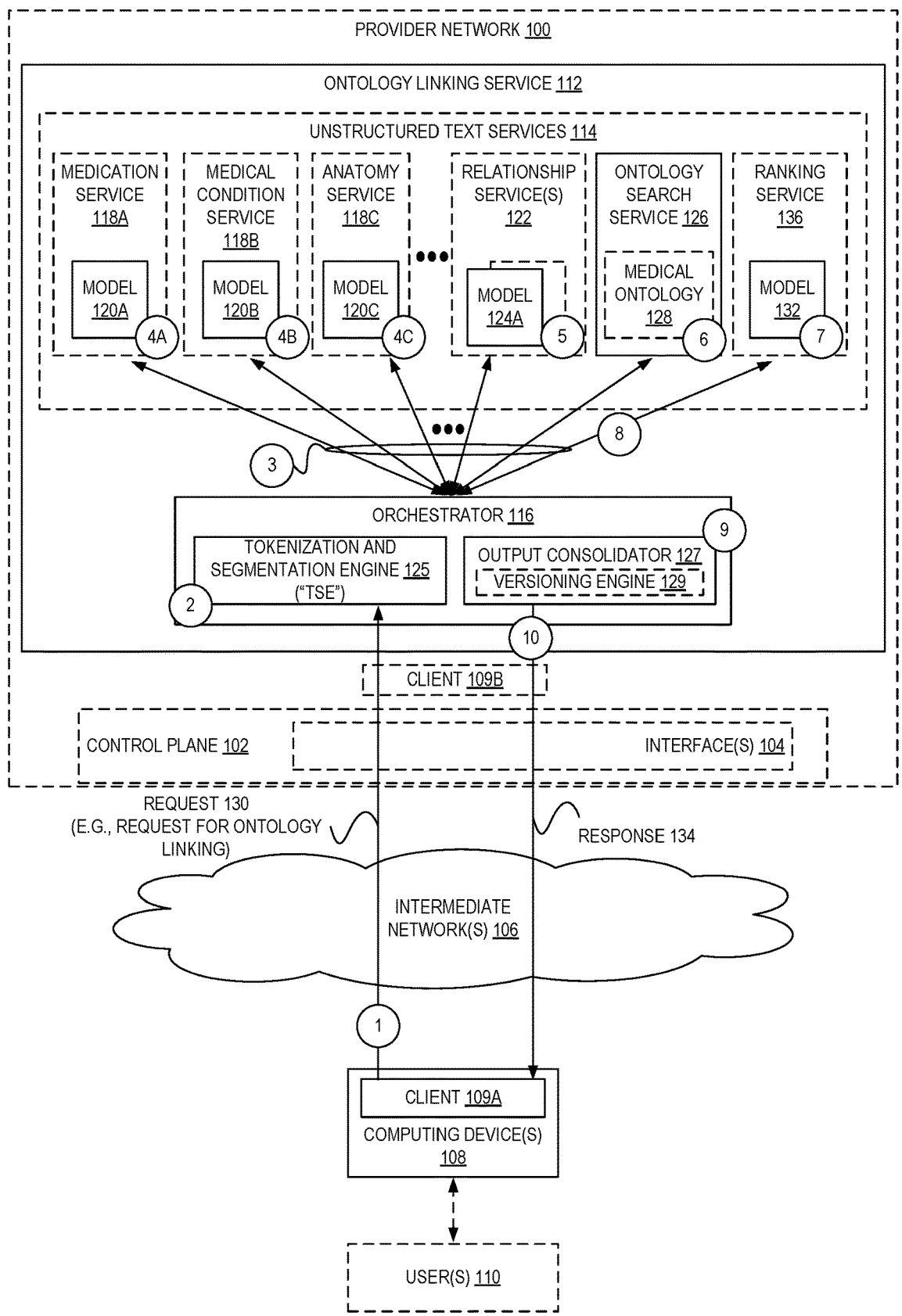
FIG. 1 is a diagram illustrating an environment for ontology linking of unstructured text according to some embodiments.

Various embodiments of methods, apparatus, systems, and non-transitory computer-readable storage media for ontology linking of unstructured text are described. According to some embodiments, a service for ontology linking is disclosed that upon a user's request can quickly and accurately identify various types of entities and relationships from unstructured text and link the entities to standardized concepts in an ontology (e.g., knowledge base of the ontology). The term ontology may generally refer to a set of concepts and categories in a subject area or domain that shows their properties and the relations between them. In one embodiment, the service receives unstructured data (e.g., unstructured text) from a client associated with the user, segments the unstructured data input and identifies entities in these segments, and provides the segmented data and entity information to be used with different machine learning (ML) models trained to detect different entity types within the segments. The output from the models may be sent to one or more other models trained to identify relationships between detected classes of objects, such as attributes and entities. The entity and relationship outputs may be used to search for a set of similar candidates from a standardized ontology (e.g., an ontology where the set of concepts and categories in a subject area or domain that shows their properties and the relations between them are defined by a particular standard). The set of similar candidates may be sent to a ranking model to rank the candidates of the set of similar candidates by their similarity to the entities (e.g., by their similarity to a set of entities forming a concept). The highest ranked candidate or candidates may be consolidated and returned to the client in a unified response. In some embodiments, the service implements various ML models trained to detect medical-related entities from unstructured text (such as doctors' notes). Clients may call the service to request that any entities, or just specific entities, of unstructured input text are identified and linked to a standardized concept or concepts from a standardized medical ontology, e.g., a medical ontology for generic and branded medication names and/or a medical ontology for medical classification codes. An example standardized medical ontology for generic and branded medication names is according to an RxNorm standard, e.g., including an RxNorm data set. An example standardized medical ontology for medical classification codes is according to an International Classification of Diseases (ICD) standard, e.g., including an International Classification of Diseases (ICD) coding scheme data set. As another example, a current ICD standard for medical classification codes is referred to as ICD-10-CM. In one embodiment, the code being output by the service is not modified from an ICD standard (e.g., not modified from an ICD-10-CM standard)

As indicated above, many organizations have large amounts of useful data stored in plaintext formats, which makes it extremely difficult to use at large scale in programmatic ways—e.g., for performing analytics. This challenge is particularly relevant in the medical field, in which there exists huge amounts of medical information—ranging from textual descriptions of symptoms, patient history, treatment plans, etc.—represented in data within plaintext fields. There remains a very strong interest in analyzing this extensive medical information to advance the field, whether for detecting optimal treatment patterns, identifying shared but unknown causes of ailments, eliminating administrative burdens, and for countless other possibilities. For example, if various notes regarding clinical trials are made in plaintext form, and a researcher seeks to identify patients who had a particular disease and took a particular medication, typically the researcher (and/or assisting workers) must examine the doctors' notes one by one and/or use search tools in complex ways, such as via crafting queries broadly enough to cover alternative spellings, abbreviations, etc., for the terms of interest, and trying to craft complex but flexible queries to search for different types of information in close proximity with other types of information, e.g., "daily" and "aspirin" and "heart attack" or "stroke" and "male" and "age 70" within some "close" amount of proximity to each other. However, this remains exceedingly difficult—for medical or administrative workers without advanced experience in information retrieval, and even for those well-versed in the field—due to the huge amount of data involved and lack of standardization in the formats of data present in these fields.

Accordingly, embodiments described herein provide a service that can be utilized in a simple and straightforward manner by clients to automatically identify entities—such as types of medications, treatments, medical conditions, etc.—and optionally, relationships involving these entities with other detected classes of objects such as attributes or traits—from unstructured text and link them to an ontology. In one embodiment, a client sends unstructured medication text to cause the service to link the medication text with a medication name from a standardized medical ontology for generic and branded medication names. Additionally or alternatively, a client may send unstructured medical condition (e.g., diagnosis) text to cause the service to link the medical condition (e.g., diagnosis) text with a medical classification code from a standardized medical ontology for medical classification codes.

As used herein, unstructured data (or unstructured information) may refer to information that either does not have a pre-defined data model or is not organized in a pre-defined manner. Thus, the term unstructured text may refer to alphanumeric type unstructured data such as one or more sentences, one or more sentence fragments, one or more paragraphs, etc. Such unstructured text is often generated or originated by humans, e.g., doctors or nurses may write notes regarding a patient, a salesperson may write notes regarding a sales lead, a student may write an essay, a lawyer may draft a contract, a transcript may be taken of a court proceeding or television broadcast, a businessperson may generate a vendor agreement, etc.

For further detail, FIG. 1 is a diagram illustrating an environment for synchronous entity and relationship detection from unstructured text according to some embodiments. In this exemplary environment, an ontology linking service 112 includes an orchestrator 116 that receives requests 130 for ontology linking of unstructured text and utilizes multiple ML models 120,124, (e.g., of a set of one or more unstructured text services 114) trained to detect particular entities and/or relationships between detected entities. In certain embodiments, the orchestrator 116 utilizes an ontology search service 126 to search for a set of similar candidates (e.g., from medical ontology 128) based on the entities and relationships. In certain embodiments, the orchestrator 116 utilizes ML model 132 to rank the set of candidates (e.g., concepts therein) of an ontology based on their similarity to entities and relationships (e.g., concepts therein).

In one embodiment, orchestrator 116 implements a "scatter" approach to processing request 130, e.g., by separately using (i) a first model (e.g., one or more of models 120A-120C) (e.g., named entity recognition model) to extract entities from the unstructured input text, (ii) a second model (e.g., model 124A) (e.g., a relationship extraction model) to find relationships between entities, (iii) a search (e.g., ontology search service 126) of an ontology (e.g., medical ontology 128) for a set of similar candidates for the entity (e.g., using a search index), and (iv) a third model (e.g., model 132) (e.g., a deep ranking model) to score the candidates by their similarity to the entity or entities from the unstructured input text. In one embodiment, orchestrator 116 serially performs four different calls (i)-(iv), respectively.

To reduce the overall latency per request, input text is chunked into segments in certain embodiments by tokenization and segmentation engine 125. Each segment can be processed in parallel to reduce the overall latency.

The outputs of the unstructured text services 114 can be used to generate a consolidated result provided as a response 134 to the request 130 that identifies the linked entity or entities from the ontology to the provided unstructured text.

In certain embodiments, detecting entities is the first step in structuring text for information retrieval. However, entity mentions by themselves may have limited use cases where they do not provide semantic knowledge on the concept they refer to. Entity linking may be used to for structuring text, e.g., where entities are linked to standardized concepts from an ontology (e.g., a knowledge base). The variability of entities that refer to the same concept, and the ambiguous entities that may refer to many concepts make this task a challenge. In healthcare, where there may be large amounts of data variation, medical ontologies provide a way for interoperability by standardizing medical concepts, their descriptions, and/or their relations to other concepts. For example, certain embodiments herein link medication(s) from input text to text (e.g., a medication name) from a standardized medical ontology for generic and branded medication names, e.g., according to an RxNorm standard. For example, certain embodiments herein link medical conditions (and/or anatomical body parts/systems) to a standardized medical ontology for medical classification codes, e.g., according to an ICD standard. In one embodiment, a standardized medical ontology is part of a unified medical language system (UMLS) developed by the United States National Library of Medicine (NLM).

In some embodiments, the ontology linking service 112 can operate to detect and link useful medical-related information in unstructured text such as clinical text to an ontology. As much as 75% of all health record data is found in unstructured text, e.g., in physician's notes, discharge summaries, test results, case notes, and so on, the ontology linking service 112 can utilize Natural Language Processing (NLP) models to sort through this enormous quantity of data, retrieve valuable information that is otherwise difficult to retrieve, and link it to an ontology without significant manual effort.

Although the ontology linking service 112 may not be a substitute for professional medical advice, diagnosis, or treatment, the ontology linking service 112 can provide confidence scores that indicate the level of confidence in the accuracy of the detected entities and/or matched concepts, which can be used to enable client systems to apply more (or less) scrutiny to its results based on the particular use case. For example, in certain use cases a client may cause the results generated by the ontology linking service 112 to be reviewed and verified by appropriately-trained human reviewers, though in other use cases such review and verification may be unnecessary or may be only needed for those results exhibiting less than some threshold amount of accuracy based on the confidence scores.

Ontology linking service is designed for simplicity such that any element that introduces unnecessary complexity, especially during maintenance, is avoided; scalability such that the it is able to scale up/out in order to support the scale that is to be handled; extendable such that it is flexible enough to be extended to support foreseeable future use cases without any need for re-architecting; efficiency to minimize the compute resources required to fulfill customer jobs; security to ensure privacy, confidentiality, and integrity of customer data, and/or availability such that it is available as long as the dependencies are available (e.g., able to tolerate intermediate failure or reasonably short outage of dependencies).

Components of the ontology linking service 112 may be implemented as software executed by one or more computing devices, as hardware, or as a combination of both hardware and software. As one example, the ontology linking service 112 may include an orchestrator 116 implemented as software executed by a first one or more computing devices and may further include one or more models 120/124/132 implemented as software by the first one or more computing devices or a second one or more computing devices.

In some embodiments, the ontology linking service 112 is implemented as a service within a provider network 100. A provider network 100 provides users with the ability to utilize one or more of a variety of types of computing-related resources such as compute resources (e.g., executing virtual machine (VM) instances and/or containers, executing batch jobs, executing code without provisioning servers), data/storage resources (e.g., object storage, block-level storage, data archival storage, databases and database tables, etc.), network-related resources (e.g., configuring virtual networks including groups of compute resources, content delivery networks (CDNs), Domain Name Service (DNS)), application resources (e.g., databases, application build/deployment services), access policies or roles, identity policies or roles, machine images, routers and other data processing resources, etc. These and other computing resources may be provided as services, such as a hardware virtualization service that can execute compute instances, a storage service that can store data objects, the ontology linking service 112 described herein, etc. Users 110 (or "customers") of provider networks 100 may utilize one or more user accounts that are associated with a customer account, though these terms may be used somewhat interchangeably depending upon the context of use. Users may utilize a computing device 108 to interact with a provider network 100 across one or more intermediate networks 106 (e.g., the internet) via one or more interface(s) 104, such as through use of application programming interface (API) calls, via a console implemented as a website or application, etc. The interface(s) 104 may be part of, or serve as a front-end to, a control plane 102 of the provider network 100 that includes "backend" services supporting and enabling the services that may be more directly offered to customers.

To provide these and other computing resource services, provider networks 100 often rely upon virtualization techniques. For example, virtualization technologies may be used to provide users the ability to control or utilize compute instances (e.g., a VM using a guest operating system (O/S) that operates using a hypervisor that may or may not further operate on top of an underlying host O/S, a container that may or may not operate in a VM, an instance that can execute on "bare metal" hardware without an underlying hypervisor), where one or multiple compute instances can be implemented using a single electronic device. Thus, a user may directly utilize a compute instance hosted by the provider network to perform a variety of computing tasks or may indirectly utilize a compute instance by submitting code to be executed by the provider network, which in turn utilizes a compute instance to execute the code (typically without the user having any control of or knowledge of the underlying compute instance(s) involved).

For example, in various embodiments, a "serverless" function may include code provided by a user or other entity that can be executed on demand. Serverless functions may be maintained within provider network 100 and may be associated with a particular user or account or may be generally accessible to multiple users and/or multiple accounts. Each serverless function may be associated with a URL, URI, or other reference, which may be used to call the serverless function. Each serverless function may be executed by a compute instance, such as a virtual machine, container, etc., when triggered or invoked. In some embodiments, a serverless function can be invoked through an application programming interface (API) call or a specially formatted HyperText Transport Protocol (HTTP) request message. Accordingly, users can define serverless functions that can be executed on demand, without requiring the user to maintain dedicated infrastructure to execute the serverless function. Instead, the serverless functions can be executed on demand using resources maintained by the provider network 100. In some embodiments, these resources may be maintained in a "ready" state (e.g., having a pre-initialized runtime environment configured to execute the serverless functions), allowing the serverless functions to be executed in near real-time. In some embodiments, one or more or all of the components of the ontology linking service 112 may be implemented as serverless functions, e.g., the orchestrator 116, tokenization and segmentation engine 125 ("TSE"), output consolidator 127, ML models 120/124/130, search service 126, etc.

As indicated herein, a user 110 may utilize the ontology linking service 112 to detect entities within medical unstructured text and link them to an ontology, e.g., medical ontology 128. Thus, the user may utilize a client 109A implemented by a computing device 108 outside the provider network 100 (e.g., as part of a medical application installed on a personal computer or server computing device, as part of a web-based console provided by the provider network 100) or a client 109B implemented by a computing device within the provider network 100 (e.g., as part of an application executed in the provider network 100, such as by a hardware virtualization service, "serverless" on-demand code execution service, etc.) to issue requests 130 at circle (1) to the ontology linking service 112.

These clients 109 may use the ontology linking service 112 for a variety of purposes. As one example, a client 109 may be part of an application allowing doctors and health care providers to manage their unstructured data effectively and rapidly assess medical information about their patients that does not easily fit into the forms traditionally used. Analyzing case notes, for instance, may help providers identify candidates for early screening for certain medical conditions linked to a standardized ontology before the condition becomes more difficult to treat. It may also allow patients to report their health concerns in a narrative that can provide more information in a simple format, and then make those narratives easily available to providers in a more structured form, allowing more accurate diagnosis, reporting, and/or billing of medical conditions.

As another example, a client 109 may operate as part of a clinical research application allowing life sciences or research organizations to optimize the matching process for fitting patients into clinical trials using information from unstructured clinical texts, such as case notes and test results. For instance, for a clinical trial of a new heart medicine, use of the ontology linking service 112 makes it much simpler to analyze text to find specific, standardized information about heart failure patients. The client 109 may also be part of an application to improve pharmacovigilance and post-market surveillance to monitor adverse drug events by using ontology linking service 112 to detect pertinent, standardized information in clinical text that is otherwise difficult to access. Moreover, the client 109 may use the ontology linking service 112 to assess therapeutic effectiveness by easily detecting vital, standardized information in follow-up notes and other clinical texts. For example, it can be easier and more effective to monitor how patients respond to certain therapies by analyzing their narratives under a standardized ontology.

As yet another example, a client 109 may be part of a medical records application, e.g., a medical billing system payor can use the ontology linking service 112 to expand its analytics to include the use of unstructured documents such as clinical notes, where information about a diagnosis is used to determine billing codes under a billing ontology.

The request 130 (and response 134) sent by clients 109 can utilize encrypted connections (e.g., using HTTPS over TLS), and the ontology linking service 112 in some embodiments does not persistently store any user/client content. Accordingly, the ontology linking service 112 may qualify as a Health Insurance Portability and Accountability Act of 1996 (HIPAA) eligible service without requiring users to configure encryption-at-rest within the service.

In some embodiments, the request 130 may be one or either of an "Infer Medication Name" (or, "InferMedicationName", e.g., "InferRXNorm") request or an "Infer Medical Classification Code" (or, "InferMedicalClassificationCode", e.g., "InferIDC10CM") request. A Infer Medication Name request may be used to indicate a client's request for the ontology linking service 112 to examine unstructured clinical text to detect textual references to medical information related to various "entities" such as medication (possibly including dosage, frequency, method of administration, etc.), treatment, etc. and link them to a standardized ontology, e.g., link the input data to a medication name (and optionally, dosage, frequency, method of administration, etc.).

In contrast, an InferMedicalClassificationCode request may be used to indicate a client's request for the ontology linking service 112 to detect references to medical information related to various "entities" such as medical condition, treatment, tests and test results, medication (possibly including dosage, frequency, method of administration, etc.), treatment, anatomy, etc., and link them to a standardized ontology, e.g., link the input data to a medical classification code. In other embodiments, other types of requests may be straightforwardly implemented by one of skill in the art based on this provided description to involve more, fewer, and/or different types of entities.

For the sake of illustration, assume the request 130 sent at circle (1) is a request for ontology linking, instructing the ontology linking service 112 to inspect provided clinical text for a variety of medical entities and return specific information linking any detected entities to an entity or entities (e.g., a set of entities forming a concept) from a standardized ontology (e.g., medical ontology 128) such as each linked entity's category, location, and/or confidence score on that information. In some embodiments, the request 130 includes an amount of unstructured text—e.g., up to 20,000 bytes of characters in some format (e.g., UTF-8). Request 130 may instruct ontology linking service 112 to first detect an entity (e.g., an entity of a particular entity type).

Figure 2:
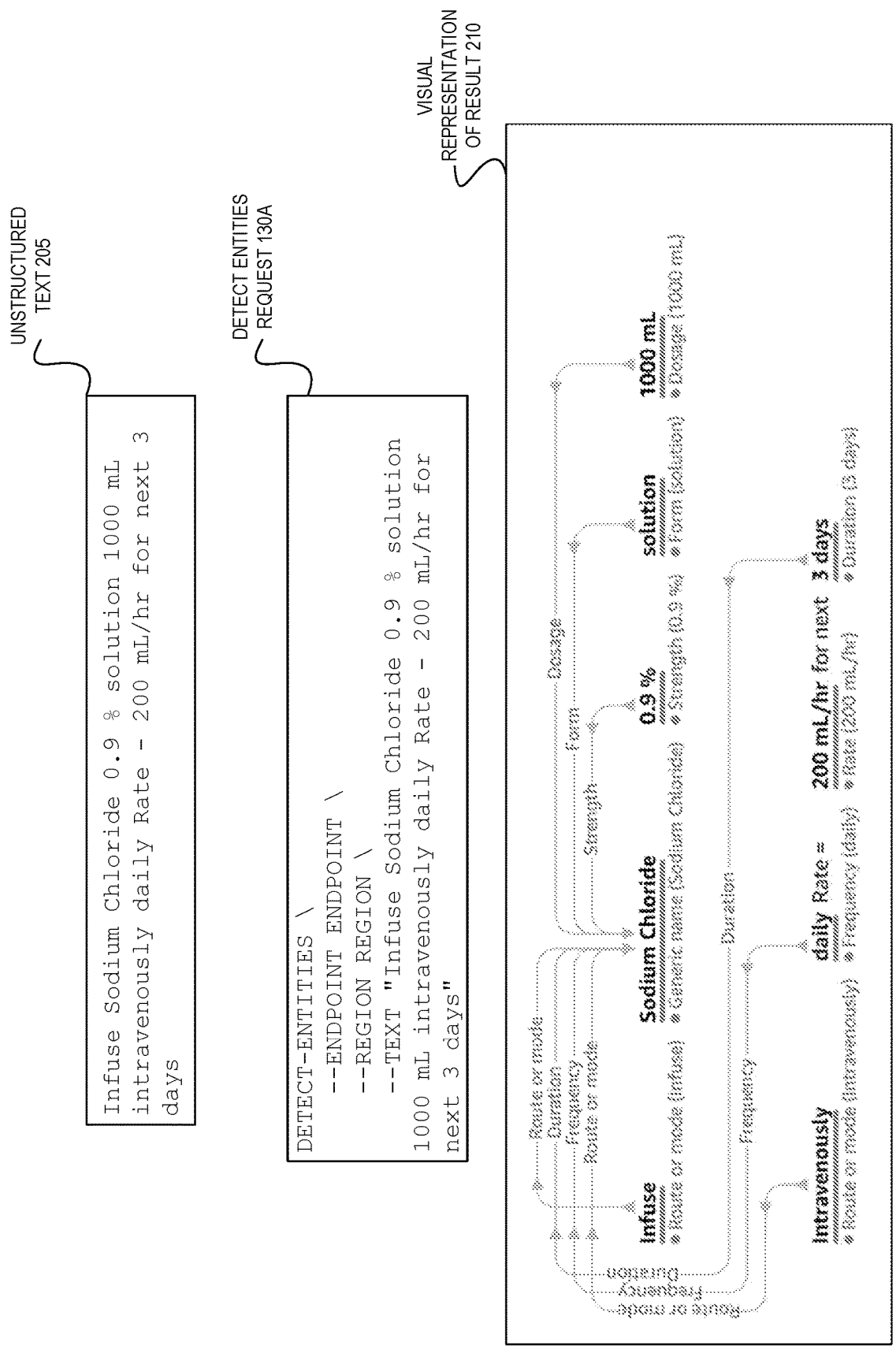
FIG. 2 is a diagram illustrating examples of medical unstructured data, an application programming interface call, and an illustration of detected entities and relationships according to some embodiments.

For example, FIG. 2 is a diagram illustrating examples of medical unstructured data, a detect entities request, and an illustration of detected entities and relationships according to some embodiments. As shown, a portion of unstructured text 205 may be submitted within the request 130 or otherwise identified by the request 130, such as via an identifier of a storage location, database record, etc., where the text is stored. In this example, the portion of unstructured text 205 reads "Infuse Sodium Chloride 0.9% solution 1000 mL intravenously daily Rate—200 mL/hr for next 3 days". This unstructured text 205 may be provided within a request, such as shown in the exemplary detect entities request 130A, which may be an API call issued to an endpoint associated with the ontology linking service 112 that identifies one or more of the service ("ontology linking service"), the method ("DETECT-ENTITIES"), an endpoint, a region, and/or the text itself.

Turning back to FIG. 1, the request 130 can be provided to an orchestrator 116 implementing a "frontend" of the service. The orchestrator 116 in some embodiments is implemented by a fleet of multiple compute instances, where each compute instance may implement one or both of a TSE 125 and an output consolidator 127. Thus, in some embodiments, the requests 130 may be load balanced between multiple such orchestrator 116 instances (or TSE 125 instances).

Upon receipt of each request by the orchestrator 116, the request 130 (or elements thereof, such as the text) may be provided to a TSE 125 at circle (2). Each TSE 125 may split the text into one or more segments, which may be based on applying a set of rules that indicate where the text is to be split. For example, the segmentation may include splitting the text based on the existence of newline characters, periods, and/or other delimiters, to yield a set of one or more segments.

In some embodiments, the TSE 125 then tokenizes the segments to identify one or more "tokens" within each segment. A token may be a word or a grouping of characters, and the tokenization may be performed by applying another set of rules that indicate where the segment is to be split. For example, the tokenization may include identifying the existence of spaces, tabs, column delimiters (such as pipes or colons), etc., to thus identify the beginning and end of a token. Thus, the TSE 125 may generate token metadata indicating a beginning location and an ending location of a token (within a segment) or a character length. Thus, for an example segment "Infuse Sodium Chloride 0.9% solution", a token of "Infuse" may be identified via a beginning offset of "0" and an ending offset of "6," or via a beginning offset of "0" and a length of "6." Likewise, a token of "0.9%" (as one example way of tokenizing including the "%" character) may be identified via a beginning offset of "23" and an ending offset of "28," or via a beginning offset of "23" and a length of "5."

In some embodiments, each identified segment of text and metadata identifying the tokens therein is provided, by the orchestrator 116, to multiple ML models 120A-120C according to a "scatter" type technique as reflected by circle (3). Each of the ML models 120A-120C may be trained to detect a particular entity type from within unstructured text, and in some cases, ones of the models 120 may be executed in parallel for a same segment or group of segments. In this example, the orchestrator 116 is shown as utilizing three models 120A-120C, though in other embodiments more or fewer models (e.g., via more or fewer services 118A-118C, respectively) may be used.

As illustrated, each ML model 120 may be implemented as part of a service (or "micro-service") that receives inference requests, optionally pre-processes the input data, provides the provided input (or pre-processed input) to an ML model trained to identify a particular type of entity, optionally post-processes the output inference result, and returns the (optionally post-processed) inference result to the client—here, the orchestrator 116. In this example system, a first model 120A may be part of a medication service 118A that identifies medications and/or dosage information at (4A), a second model 120B may be part of a medical condition service 118B that identifies symptoms and diagnosis of medical conditions at (4B), and a third model 120C may be part of an anatomy service 118C that detects references to the parts of the body or body systems and the locations of those parts or systems at (4C).

In some embodiments, one or more of the ML models 120 are trained using annotated training data, e.g., doctors' notes that have been annotated by humans and/or automated processes (e.g., active learning techniques) and the like, to cause the ML models 120 to be able to detect particular entities types. The ML models 120 may be based on a variety of ML algorithms, such as a neural network (e.g., a Long short-term memory (LSTM) neural network or other type of Recurrent Neural Network (RNN)). The training may be performed via use of an ML service and may include the use of hyperparameter tuning techniques to create a highly accurate model. The resulting trained models, in some embodiments, are hosted by an ML service, which can deploy these models as services.

In some embodiments, the ontology linking service 112—via use of these ML models—may detect information in multiples classes (or "object types"), such as entities, categories, types, attributes, traits, etc. An entity generally refers to a textual reference to the name of relevant objects, such as people, treatments, medications, or medical conditions—for example, "Ibuprofen" may be an entity. A category generally refers to a generalized grouping to which a detected entity belongs, for example, "Ibuprofen" may be part of a MEDICATION category, where a category may be associated with a particular model 120 and thus entities of that category may be detected by that model. A type generally refers to a type of the entity detected, scoped to a category. For example, "Ibuprofen" is in the GENERIC_NAME type in the MEDICATION category. An attribute generally refers to information related to a detected entity, such as a dosage of a medication—for example, "200 mg" is an attribute of an "Ibuprofen" entity. A trait generally refers to something that the ontology linking service 112 understands about an entity, based on context. For example, a medication may have a "NEGATION" trait if it determined that a patient is not taking it.

In some embodiments, the medical condition service 118B may, via use of model 120B, detect symptoms and diagnosis of medical conditions. The output of the medical condition service 118B may contains up to two entity types and up to four traits, where one or more traits can be associated with a type. The entity types may be an "ACUITY" that provides a determination of disease instance, such as chronic, acute, sudden, persistent, or gradual, and/or a "DX_NAME" that provides all medical conditions listed. The DX_NAME type may thus include a present illness, reason for visit, medical history, review of systems, family history, or patient education. The traits may include a "DIAGNOSIS" that applies to the DX_NAME type and that provides a medical condition that is determined as a cause or result of the symptoms through physical findings, laboratory or radiological reports, or any other means that the patient may or may not have had. The traits may also include a NEGATION, which is an indication that a result or action is negative or not being performed, a SIGN, which applies to the DX_NAME type and indicates a medical condition that the physician reported, and/or a SYMPTOM, which applies to the DX_NAME type and indicates a medical condition reported by the patient.

For example, upon being provided a segment "Patient is suffering from chronic aching pain 4/10", the medical condition service 118B may return "aching pain" as a DX_NAME type of entity that is of a SYMPTOM trait type, as well as another entity of "chronic" that is of the ACUITY trait type. The medical condition service 118B may also provide associated confidence scores generated by the model 120B when detecting each entity.

This information may be returned to the orchestrator 116 in a variety of formats, such as the following exemplary format. Notably, this example shows a portion which specifies, for each detected entity, one or more of: an identifier ("Id"), a beginning offset and ending offset indicating where in the segment the entity was found, a confidence score generated by the ML model 120B, the text of the entity, a type of the entity, any found traits, etc.

```
{
    "Entities": [
        {
            "Id": 0,
            "BeginOffset": 26,
            "EndOffset": 33,
            "Score": 0.9961825013160706,
            "Text": "chronic",
            "Category": "MEDICAL_CONDITION",
            "Type": "ACUITY",
            "Traits": [ ]
        },
        {
            "Id": 1,
            "BeginOffset": 34,
            "EndOffset": 45,
            "Score": 0.8380221724510193,
            "Text": "aching pain",
            "Category": "MEDICAL_CONDITION",
            "Type": "DX_NAME",
            "Traits": [
                {
                    "Name": "SYMPTOM",
                    "Score": 0.6004688739776611
                }
            ]
        }
    ],
    "UnmappedAttributes": [ ]
}
```

In some embodiments, the anatomy service 118C may, via use of model 120C, detect references to the parts of the body or body systems and the locations of those parts or systems. The anatomy service 118C may be able to detect multiple (e.g., two) entity types, such as a DIRECTION entity, which is a directional term such as left, right medial, lateral, upper, lower, posterior, anterior, distal, proximal, contralateral, bilateral, ipsilateral, dorsal, ventral, and so on, and/or a SYSTEM_ORGAN_SITE entity, which is a body system, anatomic location or region, and/or body site. As an example, with unstructured text input of "Patient's left lung", the anatomy service 118C may identify "left" as an entity of DIRECTION type and "lung" as an entity of SYSTEM_ORGAN_SITE type. As another example, with unstructured text input of "left chest pain", the anatomy service 118C may identify "left" as an entity of DIRECTION type and "chest" as an entity of SYSTEM_ORGAN_SITE type (e.g., medical condition service 118B identifying "pain" as a DX_NAME type of entity that is of a SYMPTOM trait type).

In some embodiments, the medication service 118A may, via use of model 120A, detect medication and dosage information for a patient. The medication service 118A, in response to a request, may return information that may include some or all of two entity types, seven attributes, and one trait. One or more attributes can apply to an entity type. The entity types may include a BRAND_NAME, which is a (e.g., copyrighted) brand name of the medication or therapeutic agent, or a GENERIC_NAME, which is a non-brand name, ingredient name, or formula mixture of the medication or therapeutic agent. The attributes may include one or more of a DOSAGE attribute representing an amount of medication ordered, a DURATION attribute representing how long the medication should be administered, a FORM attribute representing a form of the medication, a FREQUENCY attribute representing how often to administer the medication, a RATE attribute representing an administration rate of the medication (e.g., for medication infusions or IVs), a ROUTE_OR_MODE attribute representing the administration method of a medication, a STRENGTH attribute for medication infusions or IVs a medication strength, etc. One or more traits may also be detected, such as a NEGATION trait identifying whether there exists an indication that the patient is not taking a medication.

In some embodiments, upon receiving the detected information back from a service (e.g., the medication service 118A), the orchestrator 116 may send this information (optionally along with other information received from other models/services) for the segment to one or more relationship services 122 that utilize one or more relationship models 124A-124N to detect relationships between these entities (or other types of information) at circle (5). These relationship models may be, for example, neural networks such as (e.g., piecewise span) Convolutional Neural Networks (CNNs) trained with labeled training data indicating relationships between entities and attributes, etc. A neural network may use the spans before and after the entities as well as between them. Spans may be represented as the combination of word, position, and entity embeddings. Certain embodiments herein utilize multiple span-wise CNN layers sharing weights which are then concatenated, followed by fully connected layers, e.g., using multiple spans so that different spans can contribute differently depending upon the segment.

In some embodiments the orchestrator 116 sends results obtained from the medication service 118A to a relationship service 122 to cause the relationship service 122 to identify relationships between the detected information—e.g., which attributes belong to (or, are associated with) which entities. In some embodiments, relationship service 122 detects and classifies the semantic relations between detected entities by relation extraction. This relationship information can be used to generate more detailed results back for the requesting client, allow for more sophisticated exploration or searching of the data, etc. For example, by detecting that an attribute of "80 mg" and an attribute of "daily" is associated with an entity of "Aspirin" in the unstructured text "The patient has been daily taking 80 mg of Aspirin", a client or user may then be able to identify this record when searching for all people who take 80 mg of Aspirin daily, but not identify the record when searching for similar but different things, such as people who take 80 mg of Furosemide daily.

For example, continuing the example provided earlier regarding unstructured text of (or including) "Infuse Sodium Chloride 0.9% solution 1000 mL intravenously daily Rate—200 mL/hr for next 3 days" received in/with a request 130, this segment (along with token information) may be passed at circle (3) to multiple services 118 (e.g., services 118A-118C), and in this case the intermediate results returned from the medication service 118A may indicate that multiple entities (and/or attributes) were found with a threshold amount of confidence, and thus the orchestrator may send on those intermediate results with the segment to a relationship service 122 to identify which attributes correspond to which entities. As shown in the visual representation 210 shown in FIG. 2, this may result in the orchestrator being able to determine that a number of attributes are all related to the "Sodium Chloride" entity—"Infuse" is a "route or mode" attribute, "0.9%" is a strength attribute, "solution" is a form attribute, "1000 mL" is a dosage attribute, "Intravenously" is a route or mode attribute, "daily" is a frequency attribute, and "3 days" is a duration attribute. This visual representation 210 may be provided to the client (or data enabling the client to generate such a visual representation), enabling the client to present this visualization 210 to a user.

For further detail, FIG. 3 is a diagram illustrating an abbreviated example result 300 including detected entities and relationships according to some embodiments. For example, in some embodiments the result includes an entry or node for each detected entity. Each Entity may include an array of Attributes extracted that relate to the entity, a BeginOffset integer that provides the 0-based character offset in the input text that shows where the entity begins, a string Category indicating what type the entity is (e.g., MEDICATION, MEDICAL_CONDITION, PROTECTED_HEALTH_INFORMATION, TEST_TREATMENT_PROCEDURE, ANATOMY, which correspond to models 118/services 118), an EndOffset integer that provides the 0-based character offset in the input text that shows where the entity ends, an Id integer that is a monotonically increasing identifier unique within this response rather than a global unique identifier, a Score float that indicates a level of confidence that the ontology linking service has in the accuracy of the detection (based on an accuracy/confidence score provided by the respective detecting model), a Text string indicating the segment of input text extracted as this entity, an array of Traits providing contextual information for the entity, a Type string describing the specific type of entity.

Each Attribute may similarly include a BeginOffset integer, an EndOffset integer, an Id, a RelationshipScore float indicating a level of confidence that the ontology linking service has that this attribute is correctly related to the particular entity, a Score float indicating the level of confidence that ontology linking service has that the segment of text is correctly recognized as an attribute, a Text string, an array of Traits, a Type string, etc. Each Trait may include, for example, a Name string providing a name or contextual description about the trait, a Score float indicating a level of confidence that ontology linking service 112 has in the accuracy of this trait, etc.

This information can be beneficially used in a variety of ways. For example, for the unstructured text "Aspirin 100 mg Sodium Chloride 1000 ml", but Aspirin and Sodium Chloride may be recognized as being potentially associated with both 100 mg and 100 ml; however, it would likely be the case that 100 mg would be associated with Aspirin with a very high RelationshipScore and associated with 1000 ml with a very low RelationshipScore (the same, but in the inverse, would likely be true for Sodium Chloride). Thus, embodiments can beneficially provide for various confidences in the detected relationships, which could potentially be used by a client in different ways depending on the context of use.

In FIG. 3, this example (abbreviated) result 300 is shown for the unstructured text "Infuse Sodium Chloride 0.9% solution 1000 mL intravenously daily Rate—200 mL/hr for next 3 days". In this case a top-level entity (of ID=1) exists for "Sodium Chloride" of the MEDICATION category. This entity has multiple attributes—two of which are represented here for the sake of illustration—one for the text "INFUSE" and one for the text "3 DAYS", each having an identified type of attribute, a score, etc. In this case, another set of unmapped attributes are also presented. Such unmapped attributes are those attributes that are unable to be "mapped" to a particular entity with a sufficient amount (e.g., threshold) of confidence, though the attribute itself was found with some threshold amount of confidence. In this example, a medication attribute of "1000 ML" was found as well as a medication attribute of "200 ML/HR".

In certain embodiments, after determining which entities are related, ontology linking service 112 groups them together. For medication category, ontology linking service 112 may concatenate the name, strength, form and brand name entities, e.g., for linked, detected entities of Chlorhexidine (GENERIC_NAME), 4% (STRENGTH), solution (soln.) (FORM), "Chlorhexidine" will be concatenated with "4%" and "soln". Next, ontology linking service 112 may search at circle (6) for similar candidates in the ontology using search service 126. After candidate selection, ontology linking service 112 may rank at circle (7) the candidates based on their similarity (e.g., ranked by a similarity score) to the concatenated medication entity, and provide an indication for the ranked entities (e.g., ranked concept of multiple concepts) at circle (8). One embodiment of a ranking model is a deep learning model trained on an unlabeled clinical note corpus, e.g., and adding a dense layer to generate a similarity score, and use max-margin ranking loss to maximize the difference between positive candidates and negative candidates.

With the intermediate results obtained from each utilized service—e.g., results from one or more of services 118A-118C, one or more of relationship service(s) 122, ontology search service 126, and ranking service 136 for a request 130,—an output consolidator 127 may operate upon these intermediate results to generate a single result at circle (9) (e.g., based at least partially on these intermediate results) that can be returned to the client 109 via a response 134 at circle (10).

For example, in some embodiments when the processing is successful, the response is sent back as a HTTP 200 response that carries JSON formatted data. This data may include a collection of the medical entities extracted from the input text and their associated information. In one embodiment, for each detected entity in the input text, the response provides the detected entity text, the entity category, where the entity text begins and ends, the level of confidence in the detection and analysis, and/or the matched entity or entities (e.g., concept or concepts) from the standardized ontology. Attributes and traits of the entity may also be returned.

In some embodiments, the output consolidator 127 may include a versioning engine 129 that can be utilized to generate a model version token that may be included in the response 134. In some cases, especially when the versions of the models 120/124/132 may be occasionally or continually updated or changed over time, a model version token may be provided in a response that can be used to identify which versions of which models were utilized to generate the result. The model version token may be generated based on model version identifiers corresponding to software release versions of the models—e.g., a concatenation of model version numbers is generated and then encrypted, etc. In such an example, the client/user may be unable to decrypt or de-obfuscate the model version token, though it could be provided back to the operator of the ontology linking service 112 who is in possession of the token generation logic and/or key used to encrypt the model version numeric data (e.g., when 2-way encryption is used). Such a scheme enables, for example, the operator of the ontology linking service 112 to analyze some problematic or unexpected output generated by the ontology linking service 112 by, among other things, determining which exact versions of the involved model(s) were utilized to generate that result.

The ultimate response can be presented to a user, utilized by an application, persisted for later use, etc.

Figure 4A:
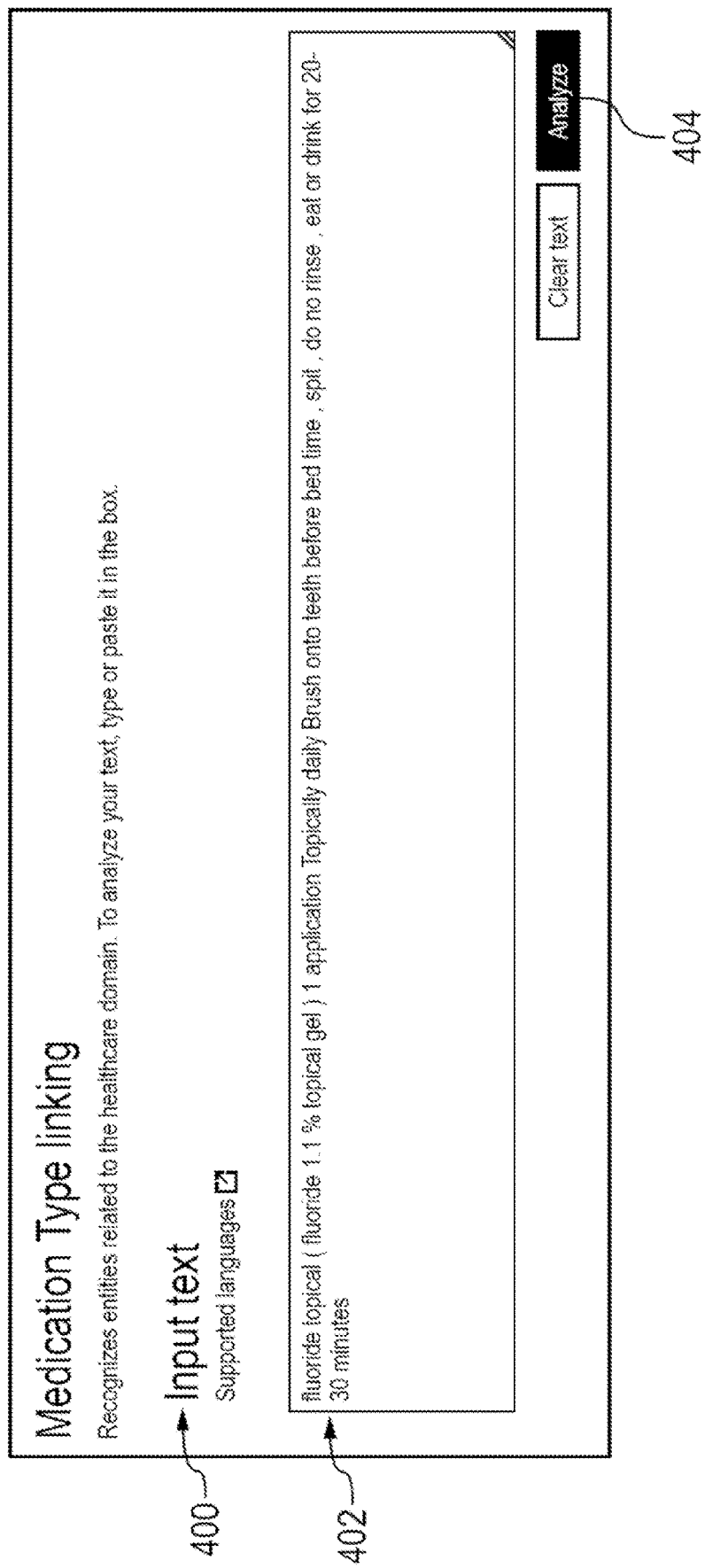
FIG. 4A is a diagram illustrating an exemplary graphical user interface for inputting unstructured text for a request to link the input text with a medical ontology according to some embodiments.

FIG. 4A is a diagram illustrating an exemplary graphical user interface 400 for inputting unstructured text 402 for a request to link the input text with a medical ontology according to some embodiments. In one embodiment, a user enters the unstructured text 402 and then selects analyze 404 (e.g., an analyze button) to begin the process of linking the unstructured text to an ontology.

FIG. 4B is a diagram illustrating an exemplary graphical user interface 406 of results of the request in FIG. 4A for presenting the detected entities and a matched concept 408 from the medical ontology according to some embodiments. Ontology linking request has returned results that identify fluoride (type=generic_name), topical (type=route or mode), 1.1% (type=strength), and topical gel (type=form) from the unstructured text 402 that is input in FIG. 4A. Ontology linking request has also indicated a matched concept 408 from the medical ontology. The format of the matched concept 408 may thus be a standardized format (e.g., as depicted).

FIG. 4C is a diagram illustrating another exemplary graphical user interface 410 of results of the request in FIG. 4A for presenting matched concepts 412, 414 for detected entities from the medical ontology according to some embodiments. Ontology linking request has returned result 412 that identifies the top five (although one or any plurality of concepts may be returned as results in certain embodiments) inferred concepts from the medical ontology for the "(fluoride 1.1% topical gel)" detected entities from the unstructured text 402 that is input in FIG. 4A. Ontology linking request has returned result 414 that identifies the top five (although one or any plurality of concepts may be returned as results in certain embodiments) inferred concepts from the medical ontology for the "fluoride topical" detected entities from the unstructured text 402 that is input in FIG. 4A. Matched concepts may be ranked in order of descending score as depicted. The ID number (e.g., 1486566 for the first concept in matched concepts 412) may be a concept ID number.

FIG. 5A is a diagram illustrating an exemplary API call 500 for inputting unstructured text for a request to link the input text with a medical ontology according to some embodiments.

FIG. 5B is a diagram illustrating an exemplary API response of results of the request in FIG. 5A for presenting the matched concepts 504, 506, 508 from the medical ontology according to some embodiments. In FIG. 5B, the three matched concepts from a medical ontology (for example, standardized medical ontology for generic and branded medication names, e.g., RxNorm standard) are returned along with their score (e.g., where a higher number indicates more similarity to a concept from the medical ontology). Thus, matched concept 504 has the highest score and is the highest ranked candidate. In one embodiment, matched concept 504 (e.g., having the entities depicted) is returned as the result of the ontology linking request, e.g., as shown in FIG. 4B or FIG. 4C. A concept identification (ID) value may also be used to track a particular concept.

Figure 6:
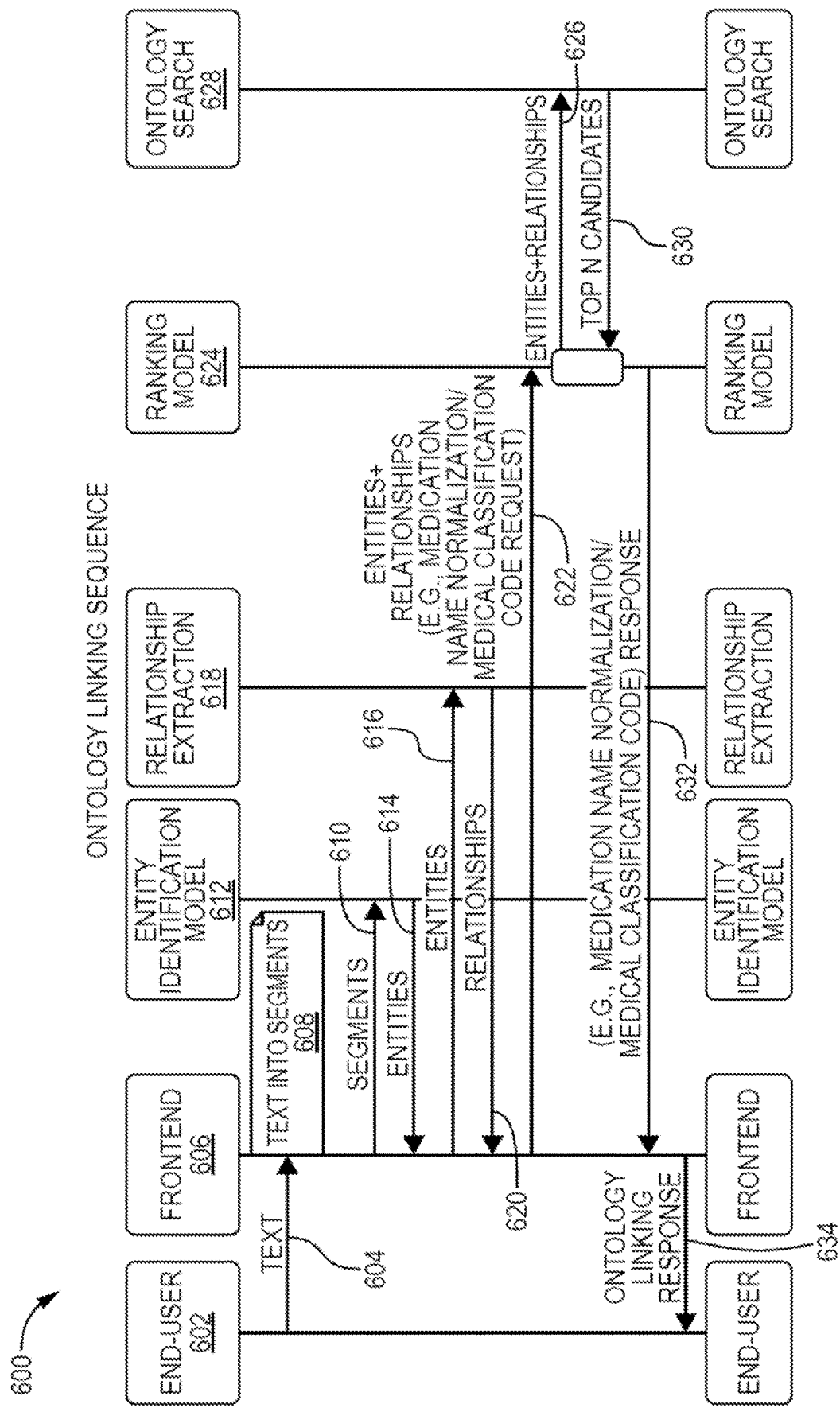
FIG. 6 is a flow diagram illustrating operations of a method for linking entities from unstructured text to an ontology according to some embodiments.

FIG. 6 is a flow diagram 600 illustrating operations of a method for linking entities from unstructured text to an ontology according to some embodiments. In one embodiment, the method includes receiving, at a frontend 606 (e.g., web service endpoint of a provider network), a request to link unstructured text to a standardized ontology, the request being originated by an end-user 602 (e.g., client) and including the unstructured text 604; identifying a plurality of segments 608 within the unstructured text; sending the plurality of segments 610 to an entity identification model 612 (e.g., a service within the provider network where the entity identification service utilizes a machine learning model 612 trained to detect entities of a particular entity type within the plurality of segments); receiving a response 614 from the entity identification model 612 identifying detected entities within the plurality of segments; sending the detected entities 616 to a relationship extraction model 618 (e.g., a relationship identification service within the provider network where the relationship identification service utilizes a machine learning model 618 trained to detect relationships between entities); receiving a response from the relationship extraction model 618 identifying one or more relationships 620 between the detected entities; sending the detected entities and the one or more relationships 622 to an ontology search service 628 (e.g., within the provider network), for example, by first sending the detected entities and the one or more relationships 622 to a ranking model 624 that is to then send the detected entities and the one or more relationships 626 to the ontology search 628; receiving a response from the ontology search service 628 identifying a set of similar candidates 630 (e.g., the top N candidates, where N is a positive integer) from the standardized ontology for the detected entities; sending the set of similar candidates to a ranking model 624 (e.g., a ranking service that utilizes a machine learning model 624 trained to rank candidates according to their similarity to entities); receiving a response 632 from the ranking service identifying a ranking of the set of similar candidates from the standardized ontology according to their similarity to the detected entities within the unstructured text; generating a result based at least in part on the ranking, the result identifying at least one highest ranked candidate, of the set of similar candidates from the standardized ontology, for the detected entities within the unstructured text; and sending a response 634 to the client, the response including the result. In certain embodiments, if no candidates are returned, the response 634 indicates that (e.g., "no candidates found").

In certain embodiments, the frontend service (e.g., in FIG. 6, 8, or 10) is responsible for user authentication, access control, throttling and basic input validation, segmentation, and/or tokenization of input text. In one embodiment, each segment is processed by the backend services (e.g., unstructured text services 114, including, but not limited to services implementing 612, 618, 624, and 628 in FIG. 6) in parallel (scatter gather) to provide the corresponding ontology linking response.

In certain embodiments, each request from frontend is to call four different endpoints serially. For example, each segment will go through an entity identification model (e.g., Rx/Dx model 612) to get mediation/diagnoses entities, respectively, then to relationship model to get the relationships, then to ontology search to get the top N candidates, and then through the ranking model to get normalized concepts. To reduce the overall latency per request, input text will be chunked into segments in certain embodiments such that each segment is processed in parallel.

In certain embodiments, the input API (e.g., as in FIG. 4A) is how a customer (e.g., user) interacts with the ontology linking service, e.g., where an authenticated/authorized user establishes a network connection with the API service and sends a create/describe/list/stop job(s) request following the specifications of the API. In some embodiments, the user synchronously gets a response from the service containing the result of the request.

In certain embodiments, the trust boundaries of the service for a customer include that: an unauthenticated/unauthorized user will not be able to interact with the system, only an authenticated/authorized user will be able to send a create/describe/list/stop job(s) request, an authenticated/authorized user will have visibility only into jobs under their account, and/or an authenticated/authorized user will only be able to view limited error messages emitted from the API service.

Figure 7:
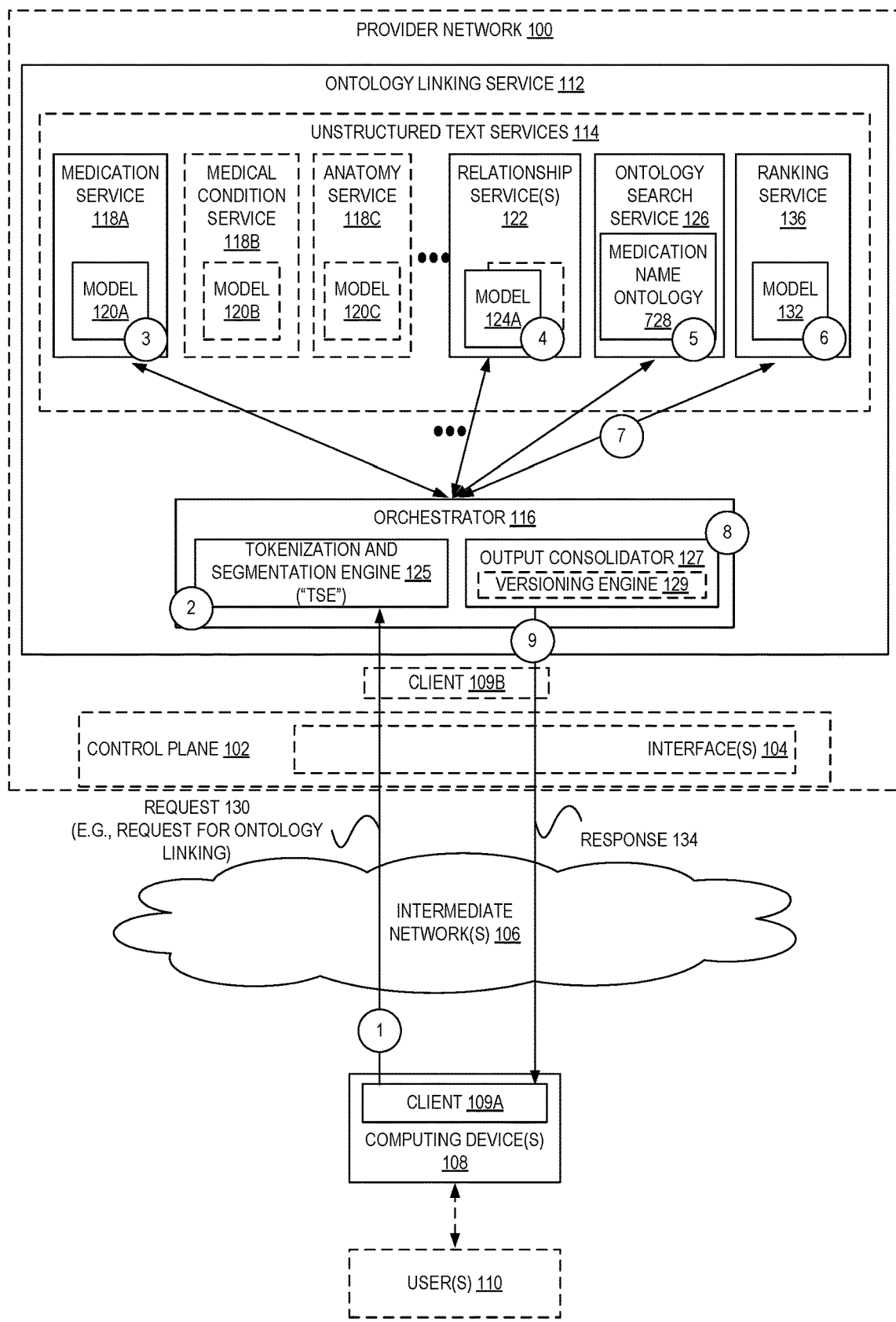
FIG. 7 is a diagram illustrating an environment for linking of unstructured text to a medication name ontology according to some embodiments.
Figure 8:
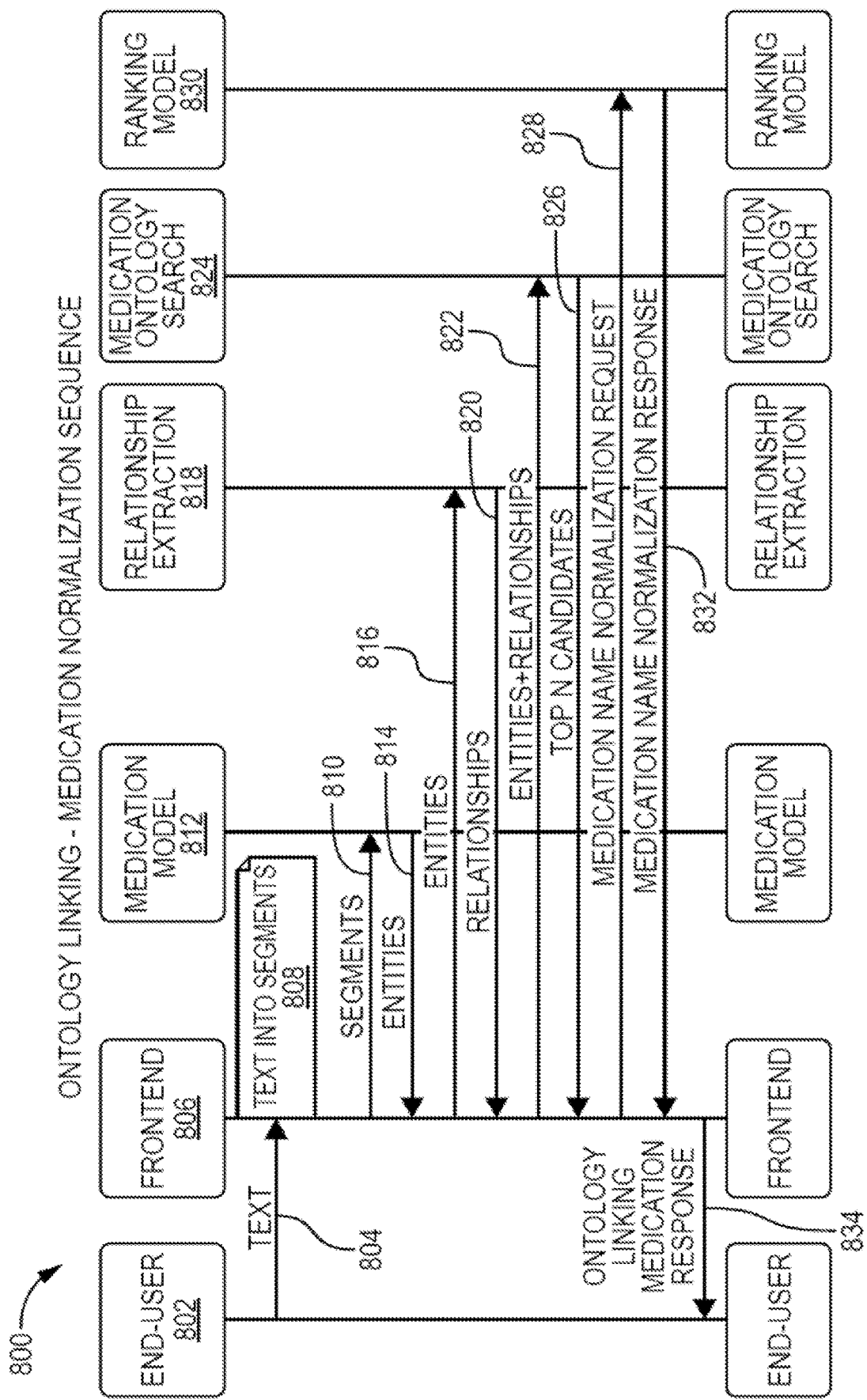
FIG. 8 is a flow diagram illustrating operations of a method for linking entities from unstructured text to a medication name ontology according to some embodiments.
Figure 9:
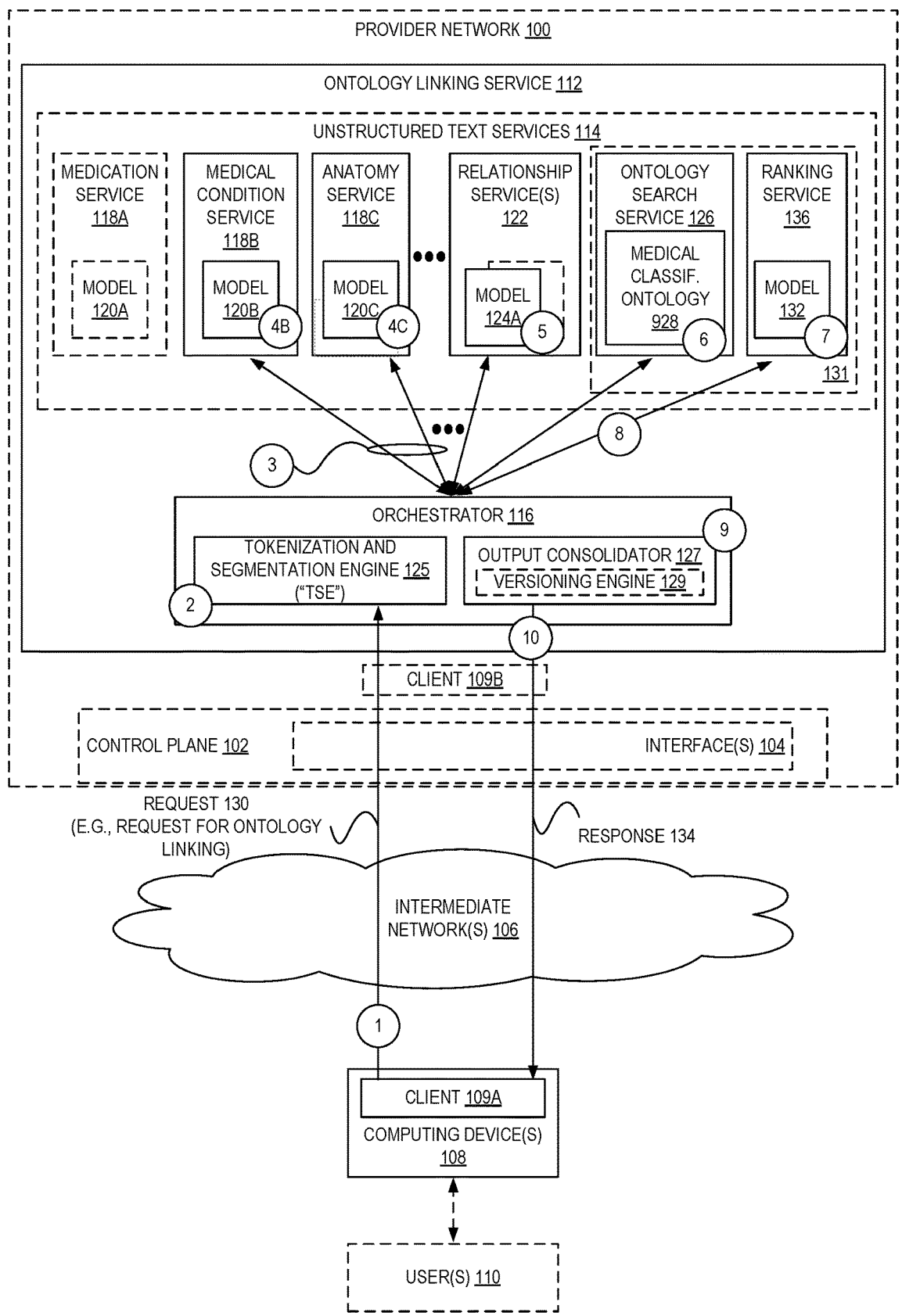
FIG. 9 is a diagram illustrating an environment for linking of unstructured text to a medical classification ontology according to some embodiments.
Figure 10:
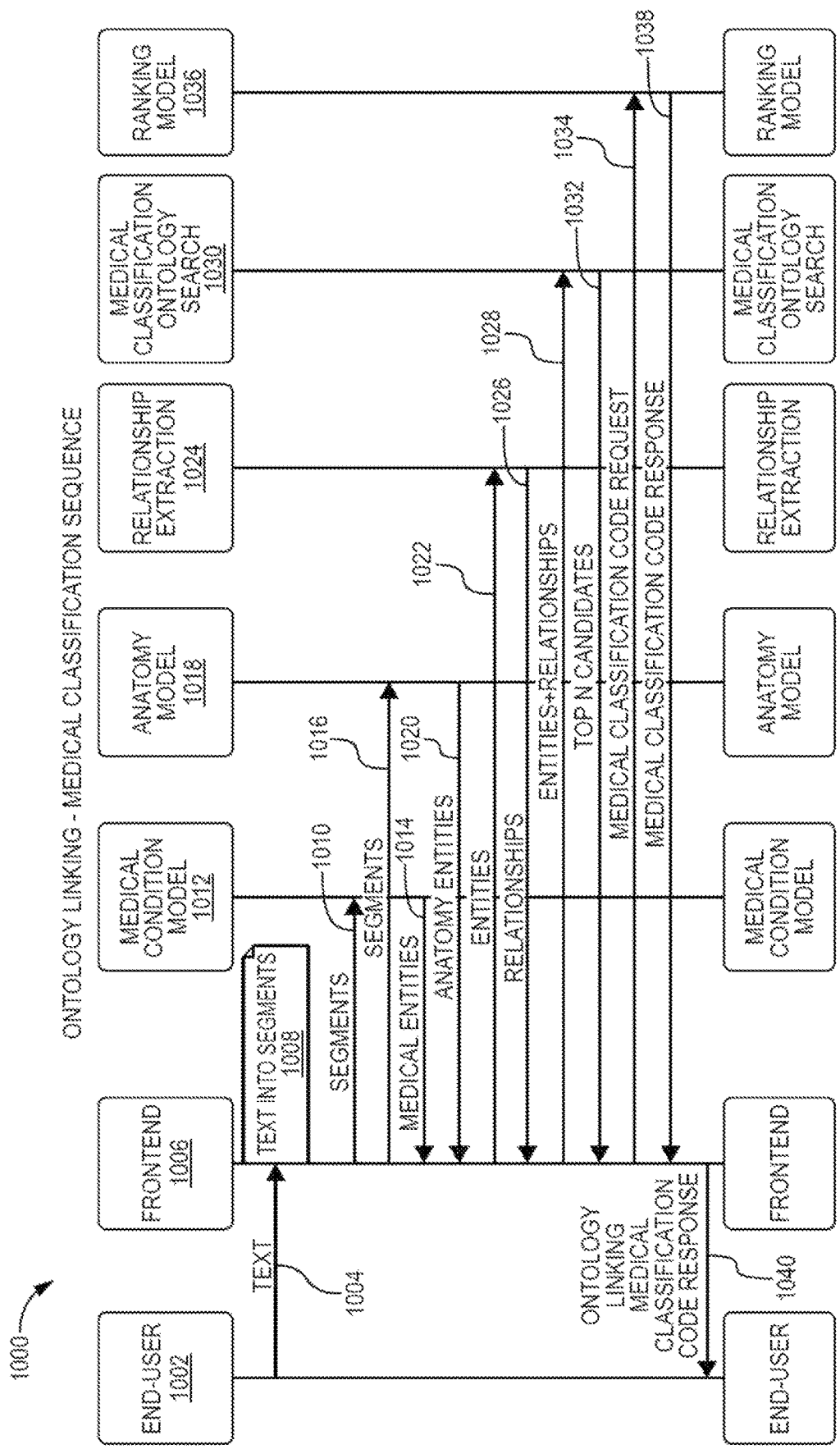
FIG. 10 is a flow diagram illustrating operations of a method for linking entities from unstructured text to a medical classification ontology according to some embodiments.

FIGS. 7-8 illustrate embodiments of linking unstructured text to a medication name ontology and FIGS. 9-10 illustrate embodiments of linking unstructured text to a medical classification (e.g., code) ontology.

FIG. 7 is a diagram illustrating an environment for linking of unstructured text to a medication name ontology 728 according to some embodiments. In one embodiment, an "Infer Medication Name" (or, "InferMedicationName", e.g., "InferRXNorm") request 130 is used to indicate a client's request for the ontology linking service 112 to examine unstructured text to detect textual references to medical information related to various medication entities (possibly including dosage, frequency, method of administration, etc.), treatment, etc. and link them to a standardized medication name (and optionally, dosage, frequency, method of administration, etc.) from medication name ontology 728.

Request 130 is to include (or otherwise identify) unstructured text, and upon receipt of the request 130 by the orchestrator 116, the request 130 (or elements thereof, such as the text) may be provided to a TSE 125 at circle (2). Each TSE 125 may split the text into one or more segments, which may be based on applying a set of rules that indicate where the text is to be split. For example, the segmentation may include splitting the text based on the existence of newline characters, periods, and/or other delimiters, to yield a set of one or more segments.

In some embodiments, the TSE 125 then tokenizes the segments to identify one or more "tokens" within each segment. A token may be a word or a grouping of characters, and the tokenization may be performed by applying another set of rules that indicate where the segment is to be split. For example, the tokenization may include identifying the existence of spaces, tabs, column delimiters (such as pipes or colons), etc., to thus identify the beginning and end of a token. Thus, the TSE 125 may generate token metadata indicating a beginning location and an ending location of a token (within a segment) or a character length.

In some embodiments, each identified segment of text (e.g., and metadata identifying the tokens therein) is provided, by the orchestrator 116, to medication ML model 120A to detect at circle (3) a medication entity type from within unstructured text, and in some cases, the model 120A may be executed in parallel for a same segment or group of segments.

In some embodiments, upon receiving the detected information back from the medication service 118A, the orchestrator 116 sends this information (optionally along with other information received from other models/services) for the segment to one or more relationship services 122 that utilize one or more relationship models 124A-124N to detect relationships between these entities (or other types of information) at circle (4). In certain embodiments, after determining which entities are related, ontology linking service 112 groups them together. For medication category, ontology linking service 112 may concatenate the name, strength, form and brand name entities, e.g., for linked, detected entities of Chlorhexidine (GENERIC_NAME), 4% (STRENGTH), solution (soln.) (FORM), "Chlorhexidine" will be concatenated with "4%" and "soln". Next, ontology linking service 112 may search at circle (5) for similar candidates in the medication name ontology 728 using search service 126. After candidate selection, ontology linking service 112 may rank at circle (6) the candidates based on their similarity (e.g., ranked by a similarity score) to the concatenated medication entity, and provide an indication for the ranked entities (e.g., ranked concept of multiple concepts) at circle (7).

With the intermediate results obtained from each utilized service—e.g., results from medication service 118A, one or more of relationship service(s) 122, ontology search service 126, and ranking service 136 for a request 130, an output consolidator 127 may operate upon these intermediate results to generate a single result (e.g., a medication name) at circle (8) (e.g., based at least partially on these intermediate results) that can be returned to the client 109 via a response 134 at circle (9).

FIG. 8 is a flow diagram 800 illustrating operations of a method for linking entities from unstructured text to a medication name ontology according to some embodiments. In one embodiment, the method includes receiving, at a frontend 806 (e.g., web service endpoint of a provider network), a request to link unstructured text to a standardized medication ontology, the request being originated by an end-user 802 (e.g., client) and including the unstructured text 804; identifying a plurality of segments 808 within the unstructured text; sending the plurality of segments 810 to a medication identification model 812 (e.g., a service within the provider network where the medication identification service utilizes a machine learning model 812 trained to detect entities of a medication entity type within the plurality of segments); receiving a response 814 from the medication identification model 812 identifying detected entities within the plurality of segments; sending the detected entities 816 to a relationship extraction model 818 (e.g., a relationship identification service within the provider network where the relationship identification service utilizes a machine learning model 818 trained to detect relationships between entities); receiving a response from the relationship extraction model 818 identifying one or more relationships 820 between the detected entities; sending the detected entities and the one or more relationships 822 to a medication ontology search service 824 (e.g., within the provider network); receiving a response from the medication ontology search service 824 identifying a set of similar candidates 826 (e.g., the top N candidates, where N is a positive integer) from the standardized medication ontology for the detected entities; sending 828 the set of similar candidates to a ranking model 830 (e.g., a ranking service that utilizes a machine learning model 830 trained to rank candidates according to their similarity to entities); receiving a response 832 from the ranking model 830 identifying a ranking of the set of similar candidates from the standardized medication ontology according to their similarity to the detected entities within the unstructured text; generating a result based at least in part on the ranking, the result identifying at least one highest ranked candidate, of the set of similar candidates from the standardized medication ontology, for the detected entities within the unstructured text; and sending a response 834 to the client, the response including the result. In certain embodiments, if no candidates are returned, the response 834 indicates that (e.g., "no candidates found").

Thus, the embodiments of linking entities from unstructured text to a medication name ontology: leverage relations to refine the scope of linking, overcomes typos, abbreviations, and lack of structure, and understands complex mapping of generic medication name with a brand medication name.

FIG. 9 is a diagram illustrating an environment for linking of unstructured text to a medical classification ontology 928 according to some embodiments. In one embodiment, an "Infer Medical Classification Code" (or, "InferMedicalClassificationCode", e.g., "InferIDC10CM") request 130 is used to indicate a client's request for the ontology linking service 112 to examine unstructured text to detect textual references to medical information related to medical condition, treatment, tests and test results, medication (possibly including dosage, frequency, method of administration, etc.), treatment, anatomy, etc. entities, and link them to a standardized medical classification code from medical classification ontology 928.

Request 130 is to include (or otherwise identify) unstructured text, and upon receipt of the request 130 by the orchestrator 116, the request 130 (or elements thereof, such as the text) may be provided to a TSE 125 at circle (2). Each TSE 125 may split the text into one or more segments, which may be based on applying a set of rules that indicate where the text is to be split. For example, the segmentation may include splitting the text based on the existence of newline characters, periods, and/or other delimiters, to yield a set of one or more segments.

In some embodiments, the TSE 125 then tokenizes the segments to identify one or more "tokens" within each segment. A token may be a word or a grouping of characters, and the tokenization may be performed by applying another set of rules that indicate where the segment is to be split. For example, the tokenization may include identifying the existence of spaces, tabs, column delimiters (such as pipes or colons), etc., to thus identify the beginning and end of a token. Thus, the TSE 125 may generate token metadata indicating a beginning location and an ending location of a token (within a segment) or a character length.

In some embodiments, each identified segment of text (e.g., and metadata identifying the tokens therein) is provided, by the orchestrator 116, to medical condition ML model 120B to detect at circle (4B) a medical classification entity type (e.g., symptoms and diagnosis of medical conditions) from within unstructured text and to an anatomy ML model 120C to detect at circle (4C) an anatomy entity type (e.g., references to the anatomical parts of the body or body systems and/or the locations of those parts or systems), and in some cases, the models 120B and 120C may be executed in parallel for a same segment or group of segments, e.g., for requests sent in parallel at circle (3).

In some embodiments, upon receiving the detected information back from the medical condition service 118B, anatomy service 120C, the orchestrator 116 sends this information (optionally along with other information received from other models/services) for the segment to one or more relationship services 122 that utilize one or more relationship models 124A-124N to detect relationships between these entities (or other types of information) at circle (5). In certain embodiments, after determining which entities are related, ontology linking service 112 groups them together. Next, ontology linking service 112 may search at circle (6) for similar candidates in the medical classification (e.g., code) ontology 928 using search service 126. After candidate selection, ontology linking service 112 may rank at circle (7) the candidates based on their similarity (e.g., ranked by a similarity score) to the (e.g., concatenated medical classification) grouped entity or entities, and provide an indication for the ranked entities (e.g., ranked concept of multiple concepts) at circle (8). In one embodiment, ontology search service 126 and ranking service 136 are combined as a single search and ranking service 131.

With the intermediate results obtained from each utilized service—e.g., results from medical condition service 118B, anatomy service 118C, one or more of relationship service(s) 122, ontology search service 126, and ranking service 136 for a request 130, an output consolidator 127 may operate upon these intermediate results to generate a single result (e.g., a medical classification code) at circle (9) (e.g., based at least partially on these intermediate results) that can be returned to the client 109 via a response 134 at circle (10).

FIG. 10 is a flow diagram 1000 illustrating operations of a method for linking entities from unstructured text to a medical classification ontology according to some embodiments. In one embodiment, the method includes receiving, at a frontend 1006 (e.g., web service endpoint of a provider network), a request to link unstructured text to a standardized medical classification ontology, the request being originated by an end-user 1002 (e.g., client) and including the unstructured text 1004; identifying a plurality of segments 1008 within the unstructured text; sending the plurality of segments 1010 to a medical condition identification model 1012 (e.g., a service within the provider network where the medical condition service utilizes a machine learning model 1012 trained to detect entities of a medical condition entity type within the plurality of segments); receiving a response 1014 from the medical condition identification model 1012 identifying detected medical entities within the plurality of segments; sending (e.g., in parallel to sending the plurality of segments to a medical condition identification model 1012) the plurality of segments 1016 to an anatomy identification model 1018 (e.g., a service within the provider network where the anatomy service utilizes a machine learning model 1018 trained to detect entities of an anatomy type within the plurality of segments); receiving a response 1020 from the anatomy identification model 1018 identifying detected anatomy entities within the plurality of segments; sending the detected medical entities and the detected anatomy entities 1022 to a relationship extraction model 1024 (e.g., a relationship identification service within the provider network where the relationship identification service utilizes a machine learning model 1024 trained to detect relationships between entities); receiving a response from the relationship extraction model 1024 identifying one or more relationships 1026 between the detected entities; sending the detected entities and the one or more relationships 1028 to a medical classification ontology search service 1030 (e.g., within the provider network); receiving a response from the medical classification ontology search service 1030 identifying a set of similar candidates 1032 (e.g., the top N candidates, where N is a positive integer) from the standardized medical classification ontology for the detected entities; sending 1034 the set of similar candidates (e.g., candidates of medical classification codes) to a ranking model 1036 (e.g., a ranking service that utilizes a machine learning model 1036 trained to rank candidates according to their similarity to entities); receiving a response 1038 from the ranking model 1036 identifying a ranking of the set of similar candidates from the standardized medical classification ontology according to their similarity to the detected entities within the unstructured text; generating a result based at least in part on the ranking, the result identifying at least one highest ranked candidate, of the set of similar candidates from the standardized medical classification ontology, for the detected entities within the unstructured text; and sending a response 1040 to the client, the response including the result. In certain embodiments, if no candidates are returned, the response 1040 indicates that (e.g., "no candidates found"). In one embodiment, ontology search 1030 service and ranking model 1036 service are combined as a single search and ranking service.

Thus, the embodiments of linking entities from unstructured text to a medical classification ontology: understands latent anatomical relations to refine the candidate concepts, complex contextual information to refine the candidate concepts, and comorbidities and related symptoms to refine the candidate concepts. For example, for an unstructured text input of "He notes the pain is localized to the left proximal metacarpal, non-radiating, four out of ten in severity. He describes it as a deep burning pain", the medical classification ontology is to return a list of candidates of "pain in left finger(s)" with a similarity score of 99%, "pain, unspecified" with a similarity score of 96%, "lower, abdominal pain, unspecified" with a similarity score of 93%, and "epigastric pain" with a similarity score of 24%. These scores can thus be used to pick the best candidates (e.g., "pain in left finger(s)" in the above example) and the billing code corresponding to the best candidate (and standardized text for that candidate such as "pain in left finger(s)") from the medical classification ontology.

Figure 11:
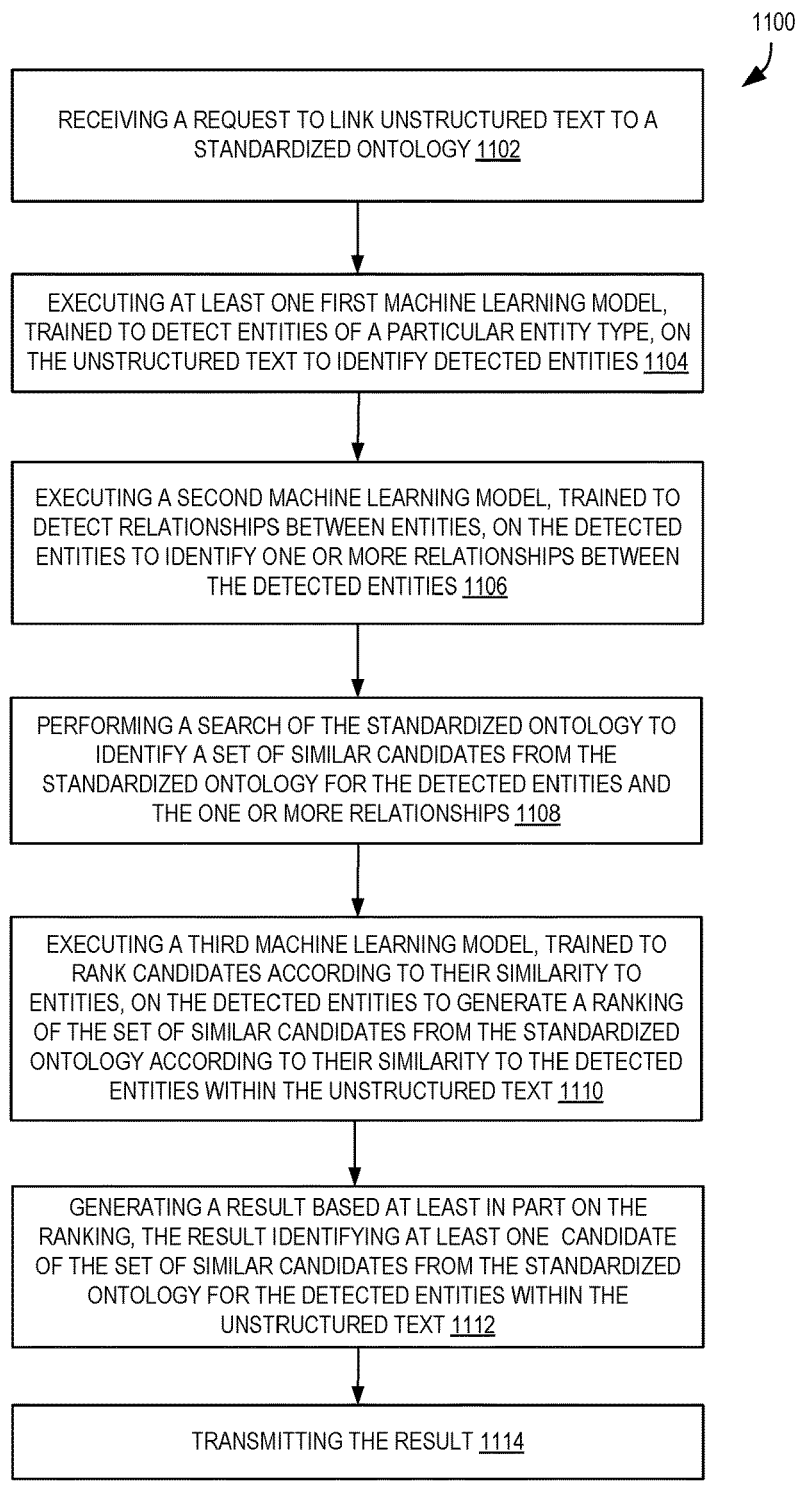
FIG. 11 is a flow diagram illustrating operations of a method for linking entities from unstructured text to an ontology according to some embodiments.

FIG. 11 is a flow diagram 1100 illustrating operations of a method for linking entities from unstructured text to an ontology according to some embodiments. Depicted flow diagram 1100 includes receiving a request to link unstructured text to a standardized ontology 1102; executing at least one first machine learning model, trained to detect entities of a particular entity type, on the unstructured text to identify detected entities 1104; executing a second machine learning model, trained to detect relationships between entities, on the detected entities to identify one or more relationships between the detected entities 1106; performing a search of the standardized ontology to identify a set of similar candidates from the standardized ontology for the detected entities and the one or more relationships 1108; executing a third machine learning model, trained to rank candidates according to their similarity to entities, on the detected entities to generate a ranking of the set of similar candidates from the standardized ontology according to their similarity to the detected entities within the unstructured text 1110; generating a result based at least in part on the ranking, the result identifying at least one candidate of the set of similar candidates from the standardized ontology for the detected entities within the unstructured text 1112; and transmitting the result 1114.

The request, in some embodiments, was originated by a client and indicates that the result is to be generated and returned to the client synchronously via a same network connection; and the transmitting of the result occurs via the same network connection.

The request, in some embodiments, was originated by a client and identifies at least a storage location where the result is to be stored; and transmitting the result comprises sending the result to a storage service to be stored at the storage location.

Figure 12:
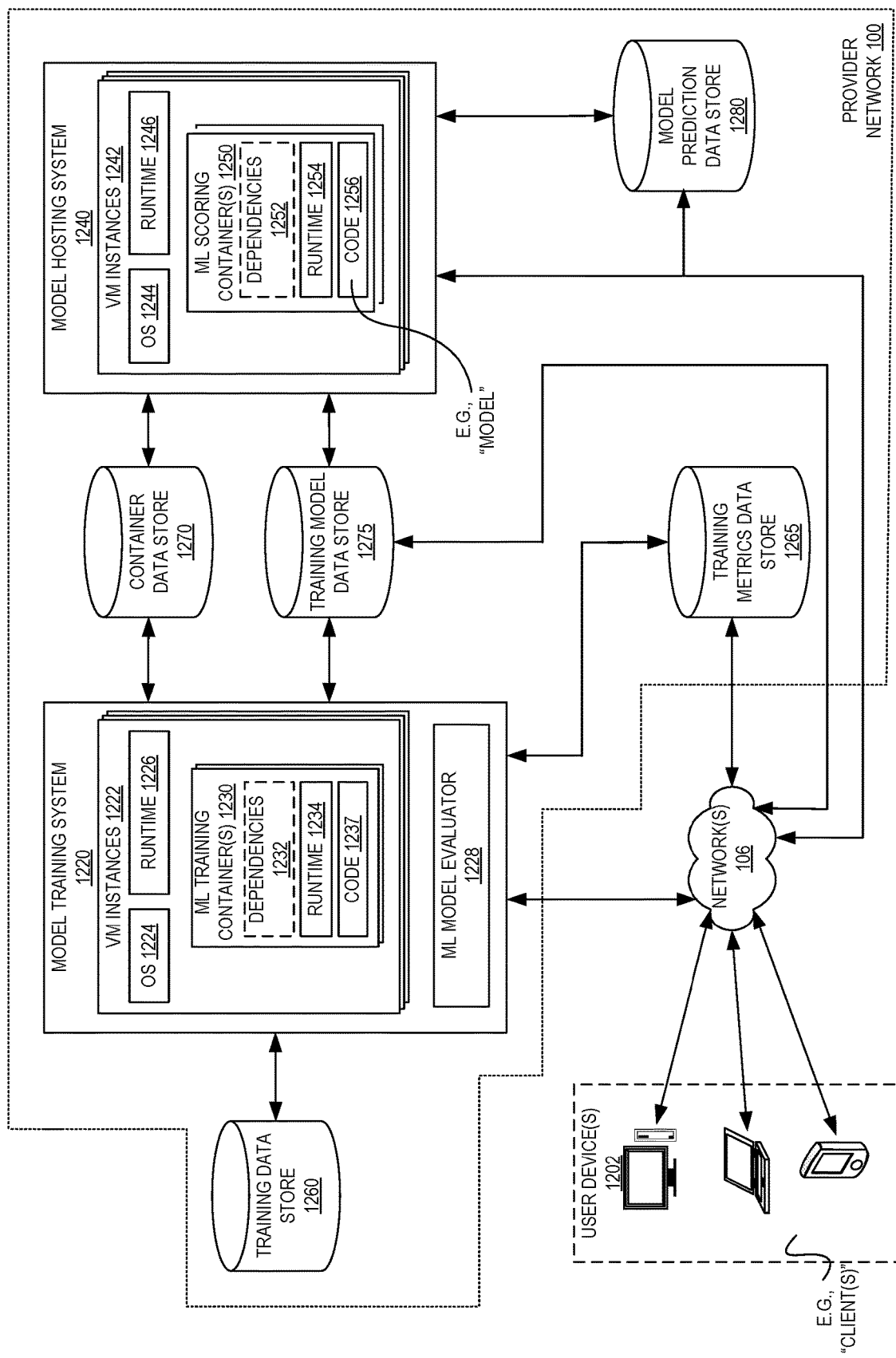
FIG. 12 is a block diagram of an illustrative operating environment in which machine learning models are trained and hosted according to some embodiments.

FIG. 12 is a block diagram of an illustrative operating environment in which ML models are trained and hosted according to some embodiments. The operating environment includes end user devices 1202 (e.g., a PC or mobile device, such as computing device(s) 108), a model training system 1220, a model hosting system 1240, a training data store 1260, a training metrics data store 1265, a container data store 1270, a training model data store 1275, and a model prediction data store 1280. An ML service described herein may include one or more of these entities, such as the model hosting system 1240, model training system 1220, etc.

In some embodiments, users, by way of user devices 1202, interact with the model training system 1220 to provide data that causes the model training system 1220 to train one or more ML models. AN ML model, generally, may be thought of as one or more equations that are "trained" using a set of data. In some embodiments, the model training system 1220 provides ML functionalities as a Web service, and thus messaging between user devices 1202 and the model training system 1220 (or provider network 100), and/or between components of the model training system 1220 (or provider network 100), may utilize HTTP messages to transfer data in a machine-readable file format, such as eXtensible Markup Language (XML) or JavaScript Object Notation (JSON).

The user devices 1202 can interact with the model training system 1220 via frontend 1229 of the model training system 1220. For example, a user device 1202 can provide a training request to the frontend 1229 that includes a container image (or multiple container images, or an identifier of one or multiple locations where container images are stored), an indicator of input data (e.g., an address or location of input data), one or more hyperparameter values (e.g., values indicating how the algorithm will operate, how many algorithms to run in parallel, how many clusters into which to separate data, etc.), and/or information describing the computing machine on which to train an ML model (e.g., a graphical processing unit (GPU) instance type, a central processing unit (CPU) instance type, an amount of memory to allocate, a type of virtual machine instance to use for training, etc.).

In some embodiments, the container image can include one or more layers, where each layer represents an executable instruction. Some or all of the executable instructions together represent an algorithm that defines an ML model. The executable instructions (e.g., the algorithm) can be written in any programming language (e.g., Python, Ruby, C++, Java, etc.). In some embodiments, the algorithm is pre-generated and obtained by a user, via the user device 1202, from an algorithm repository (e.g., a network-accessible marketplace, a data store provided by an ML training service, etc.). In some embodiments, the algorithm is completely user-generated or partially user-generated (e.g., user-provided code modifies or configures existing algorithmic code).

In some embodiments, instead of providing a container image (or identifier thereof) in the training request, the user device 1202 may provide, in the training request, an algorithm written in any programming language. The model training system 1220 packages the algorithm into a container (optionally with other code, such as a "base" ML algorithm supplemented with user-provided code) that is eventually loaded into a virtual machine instance 1222 for training an ML model, as described in greater detail below. For example, a user, via a user device 1202, may develop an algorithm/code using an application (e.g., an interactive web-based programming environment) and cause the algorithm/code to be provided—perhaps as part of a training request (or referenced in a training request)—to the model training system 1220, where this algorithm/code may be containerized on its own or used together with an existing container having an ML framework, for example.

In some embodiments, instead of providing a container image in the training request, the user device 1202 provides, in the training request, an indicator of a container image (e.g., an indication of an address or a location at which a container image is stored). For example, the container image can be stored in a container data store 1270, and this container image may have been previously created/uploaded by the user. The model training system 1220 can retrieve the container image from the indicated location and create a container using the retrieved container image. The container is then loaded into a virtual machine instance 1222 for training an ML model, as described in greater detail below.

The model training system 1220 can use the information provided by the user device 1202 to train an ML model in one or more pre-established virtual machine instances 1222 in some embodiments. In particular, the model training system 1220 includes a single physical computing device or multiple physical computing devices that are interconnected using one or more computing networks (not shown), where the physical computing device(s) host one or more virtual machine instances 1222. The model training system 1220 can handle the acquisition and configuration of compute capacity (e.g., containers, instances, etc., which are described in greater detail below) based on the information describing the computing machine on which to train an ML model provided by the user device 1202. The model training system 1220 can then train ML models using the compute capacity, as is described in greater detail below. The model training system 1220 can automatically scale up and down based on the volume of training requests received from user devices 1202 via frontend 1229, thereby relieving the user from the burden of having to worry about over-utilization (e.g., acquiring too little computing resources and suffering performance issues) or under-utilization (e.g., acquiring more computing resources than necessary to train the ML models, and thus overpaying).

In some embodiments, the virtual machine instances 1222 are utilized to execute tasks. For example, such tasks can include training an ML model. As shown in FIG. 12, each virtual machine instance 1222 includes an operating system (OS) 1224, a language runtime 1226, and one or more ML training containers 1230. Generally, the ML training containers 1230 are logical units created within a virtual machine instance using the resources available on that instance and can be utilized to isolate execution of a task from other processes (e.g., task executions) occurring in the instance. In some embodiments, the ML training containers 1230 are formed from one or more container images and a top container layer. Each container image may further include one or more image layers, where each image layer represents an executable instruction. As described above, some or all of the executable instructions together represent an algorithm that defines an ML model. Changes made to the ML training containers 1230 (e.g., creation of new files, modification of existing files, deletion of files, etc.) are stored in the top container layer. If an ML training container 1230 is deleted, the top container layer is also deleted. However, the container image(s) that form a portion of the deleted ML training container 1230 can remain unchanged. The ML training containers 1230 can be implemented, for example, as Linux containers (LXC), Docker containers, and the like.

The ML training containers 1230 may include individual a runtime 1234, code 1237, and dependencies 1232 needed by the code 1237 in some embodiments. The runtime 1234 can be defined by one or more executable instructions that form at least a portion of a container image that is used to form the ML training container 1230 (e.g., the executable instruction(s) in the container image that define the operating system and/or runtime to run in the container formed from the container image). The code 1237 includes one or more executable instructions that form at least a portion of a container image that is used to form the ML training container 1230. For example, the code 1237 includes the executable instructions in the container image that represent an algorithm that defines an ML model, which may reference (or utilize) code or libraries from dependencies 1232. The runtime 1234 is configured to execute the code 1237 in response to an instruction to begin ML model training. Execution of the code 1237 results in the generation of model data, as described in greater detail below.

In some embodiments, the code 1237 includes executable instructions that represent algorithms that define different ML models. For example, the code 1237 includes one set of executable instructions that represent a first algorithm that defines a first ML model and a second set of executable instructions that represent a second algorithm that defines a second ML model. In some embodiments, the virtual machine instance 1222 executes the code 1237 and trains all of the ML models. In some embodiments, the virtual machine instance 1222 executes the code 1237, selecting one of the ML models to train. For example, the virtual machine instance 1222 can identify a type of training data indicated by the training request and select an ML model to train (e.g., execute the executable instructions that represent an algorithm that defines the selected ML model) that corresponds with the identified type of training data.

In some embodiments, the runtime 1234 is the same as the runtime 1226 utilized by the virtual machine instance 1222. In some embodiments, the runtime 1234 is different than the runtime 1226 utilized by the virtual machine instance 1222.

In some embodiments, the model training system 1220 uses one or more container images included in a training request (or a container image retrieved from the container data store 1270 in response to a received training request) to create and initialize an ML training container 1230 in a virtual machine instance 1222. For example, the model training system 1220 creates an ML training container 1230 that includes the container image(s) and/or a top container layer.

Prior to beginning the training process, in some embodiments, the model training system 1220 retrieves training data from the location indicated in the training request. For example, the location indicated in the training request can be a location in the training data store 1260. Thus, the model training system 1220 retrieves the training data from the indicated location in the training data store 1260. In some embodiments, the model training system 1220 does not retrieve the training data prior to beginning the training process. Rather, the model training system 1220 streams the training data from the indicated location during the training process. For example, the model training system 1220 can initially retrieve a portion of the training data and provide the retrieved portion to the virtual machine instance 1222 training the ML model. Once the virtual machine instance 1222 has applied and used the retrieved portion or once the virtual machine instance 1222 is about to use all of the retrieved portion (e.g., a buffer storing the retrieved portion is nearly empty), then the model training system 1220 can retrieve a second portion of the training data and provide the second retrieved portion to the virtual machine instance 1222, and so on.

To perform the ML model training, the virtual machine instance 1222 executes code 1237 stored in the ML training container 1230 in some embodiments. For example, the code 1237 includes some or all of the executable instructions that form the container image of the ML training container 1230 initialized therein. Thus, the virtual machine instance 1222 executes some or all of the executable instructions that form the container image of the ML training container 1230 initialized therein to train an ML model. The virtual machine instance 1222 executes some or all of the executable instructions according to the hyperparameter values included in the training request. As an illustrative example, the virtual machine instance 1222 trains an ML model by identifying values for certain parameters (e.g., coefficients, weights, centroids, etc.). The identified values depend on hyperparameters that define how the training is performed. Thus, the virtual machine instance 1222 can execute the executable instructions to initiate an ML model training process, where the training process is run using the hyperparameter values included in the training request. Execution of the executable instructions can include the virtual machine instance 1222 applying the training data retrieved by the model training system 1220 as input parameters to some or all of the instructions being executed.

In some embodiments, executing the executable instructions causes the virtual machine instance 1222 (e.g., the ML training container 1230) to generate model data. For example, the ML training container 1230 generates model data and stores the model data in a file system of the ML training container 1230. The model data includes characteristics of the ML model being trained, such as a number of layers in the ML model, hyperparameters of the ML model, coefficients of the ML model, weights of the ML model, 12 and/or the like. In particular, the generated model data includes values for the characteristics that define an ML model being trained. In some embodiments, executing the executable instructions causes a modification to the ML training container 1230 such that the model data is written to the top container layer of the ML training container 1230 and/or the container image(s) that forms a portion of the ML training container 1230 is modified to include the model data.

The virtual machine instance 1222 (or the model training system 1220 itself) pulls the generated model data from the ML training container 1230 and stores the generated model data in the training model data store 1275 in an entry associated with the virtual machine instance 1222 and/or the ML model being trained. In some embodiments, the virtual machine instance 1222 generates a single file that includes model data and stores the single file in the training model data store 1275. In some embodiments, the virtual machine instance 1222 generates multiple files during the course of training an ML model, where each file includes model data. In some embodiments, each model data file includes the same or different model data information (e.g., one file identifies the structure of an algorithm, another file includes a list of coefficients, etc.). The virtual machine instance 1222 can package the multiple files into a single file once training is complete and store the single file in the training model data store 1275. Alternatively, the virtual machine instance 1222 stores the multiple files in the training model data store 1275. The virtual machine instance 1222 stores the file(s) in the training model data store 1275 while the training process is ongoing and/or after the training process is complete.

In some embodiments, the virtual machine instance 1222 regularly stores model data file(s) in the training model data store 1275 as the training process is ongoing. Thus, model data file(s) can be stored in the training model data store 1275 at different times during the training process. Each set of model data files corresponding to a particular time or each set of model data files present in the training model data store 1275 as of a particular time could be checkpoints that represent different versions of a partially-trained ML model during different stages of the training process. Accordingly, before training is complete, a user, via the user device 1202 can submit a deployment and/or execution request in a manner as described below to deploy and/or execute a version of a partially trained ML model (e.g., an ML model trained as of a certain stage in the training process). A version of a partially-trained ML model can be based on some or all of the model data files stored in the training model data store 1275.

In some embodiments, a virtual machine instance 1222 executes code 1237 stored in a plurality of ML training containers 1230. For example, the algorithm included in the container image can be in a format that allows for the parallelization of the training process. Thus, the model training system 1220 can create multiple copies of the container image provided in a training request and cause the virtual machine instance 1222 to load each container image copy in a separate ML training container 1230. The virtual machine instance 1222 can then execute, in parallel, the code 1237 stored in the ML training containers 1230. The virtual machine instance 1222 can further provide configuration information to each ML training container 1230 (e.g., information indicating that N ML training containers 1230 are collectively training an ML model and that a particular ML training container 1230 receiving the configuration information is ML training container 1230 number X of N), which can be included in the resulting model data. By parallelizing the training process, the model training system 1220 can significantly reduce the training time in some embodiments.

In some embodiments, a plurality of virtual machine instances 1222 execute code 1237 stored in a plurality of ML training containers 1230. For example, the resources used to train a particular ML model can exceed the limitations of a single virtual machine instance 1222. However, the algorithm included in the container image can be in a format that allows for the parallelization of the training process. Thus, the model training system 1220 can create multiple copies of the container image provided in a training request, initialize multiple virtual machine instances 1222, and cause each virtual machine instance 1222 to load a container image copy in one or more separate ML training containers 1230. The virtual machine instances 1222 can then each execute the code 1237 stored in the ML training containers 1230 in parallel. The model training system 1220 can further provide configuration information to each ML training container 1230 via the virtual machine instances 1222 (e.g., information indicating that N ML training containers 1230 are collectively training an ML model and that a particular ML training container 1230 receiving the configuration information is ML training container 1230 number X of N, information indicating that M virtual machine instances 1222 are collectively training an ML model and that a particular ML training container 1230 receiving the configuration information is initialized in virtual machine instance 1222 number Y of M, etc.), which can be included in the resulting model data. As described above, by parallelizing the training process, the model training system 1220 can significantly reduce the training time in some embodiments.

In some embodiments, the model training system 1220 includes a plurality of physical computing devices and two or more of the physical computing devices hosts one or more virtual machine instances 1222 that execute the code 1237. Thus, the parallelization can occur over different physical computing devices in addition to over different virtual machine instances 1222 and/or ML training containers 1230.

In some embodiments, the model training system 1220 includes an ML model evaluator 1228. The ML model evaluator 1228 can monitor virtual machine instances 1222 as ML models are being trained, obtaining the generated model data and processing the obtained model data to generate model metrics. For example, the model metrics can include quality metrics, such as an error rate of the ML model being trained, a statistical distribution of the ML model being trained, a latency of the ML model being trained, a confidence level of the ML model being trained (e.g., a level of confidence that the accuracy of the ML model being trained is known, etc. The ML model evaluator 1228 can obtain the model data for an ML model being trained and evaluation data from the training data store 1260. The evaluation data is separate from the data used to train an ML model and includes both input data and expected outputs (e.g., known results), and thus the ML model evaluator 1228 can define an ML model using the model data and execute the ML model by providing the input data as inputs to the ML model. The ML model evaluator 1228 can then compare the outputs of the ML model to the expected outputs and determine one or more quality metrics of the ML model being trained based on the comparison (e.g., the error rate can be a difference or distance between the ML model outputs and the expected outputs).

The ML model evaluator 1228 periodically generates model metrics during the training process and stores the model metrics in the training metrics data store 1265 in some embodiments. While the ML model is being trained, a user, via the user device 1202, can access and retrieve the model metrics from the training metrics data store 1265. The user can then use the model metrics to determine whether to adjust the training process and/or to stop the training process. For example, the model metrics can indicate that the ML model is performing poorly (e.g., has an error rate above a threshold value, has a statistical distribution that is not an expected or desired distribution (e.g., not a binomial distribution, a Poisson distribution, a geometric distribution, a normal distribution, Gaussian distribution, etc.), has an execution latency above a threshold value, has a confidence level below a threshold value)) and/or is performing progressively worse (e.g., the quality metric continues to worsen over time). In response, in some embodiments, the user, via the user device 1202, can transmit a request to the model training system 1220 to modify the ML model being trained (e.g., transmit a modification request). The request can include a new or modified container image, a new or modified algorithm, new or modified hyperparameter(s), and/or new or modified information describing the computing machine on which to train an ML model. The model training system 1220 can modify the ML model accordingly. For example, the model training system 1220 can cause the virtual machine instance 1222 to optionally delete an existing ML training container 1230, create and initialize a new ML training container 1230 using some or all of the information included in the request, and execute the code 1237 stored in the new ML training container 1230 to restart the ML model training process. As another example, the model training system 1220 can cause the virtual machine instance 1222 to modify the execution of code stored in an existing ML training container 1230 according to the data provided in the modification request. In some embodiments, the user, via the user device 1202, can transmit a request to the model training system 1220 to stop the ML model training process. The model training system 1220 can then instruct the virtual machine instance 1222 to delete the ML training container 1230 and/or to delete any model data stored in the training model data store 1275.

As described below, in some embodiments, the model data stored in the training model data store 1275 is used by the model hosting system 1240 to deploy ML models. Alternatively or additionally, a user device 1202 or another computing device (not shown) can retrieve the model data from the training model data store 1275 to implement a learning algorithm in an external device. As an illustrative example, a robotic device can include sensors to capture input data. A user device 1202 can retrieve the model data from the training model data store 1275 and store the model data in the robotic device. The model data defines an ML model. Thus, the robotic device can provide the captured input data as an input to the ML model, resulting in an output. The robotic device can then perform an action (e.g., move forward, raise an arm, generate a sound, etc.) based on the resulting output.

While the virtual machine instances 1222 are shown in FIG. 12 as a single grouping of virtual machine instances 1222, some embodiments of the present application separate virtual machine instances 1222 that are actively assigned to execute tasks from those virtual machine instances 1222 that are not actively assigned to execute tasks. For example, those virtual machine instances 1222 actively assigned to execute tasks are grouped into an "active pool," while those virtual machine instances 1222 not actively assigned to execute tasks are placed within a "warming pool." In some embodiments, those virtual machine instances 1222 within the warming pool can be pre-initialized with an operating system, language runtimes, and/or other software required to enable rapid execution of tasks (e.g., rapid initialization of ML model training in ML training container(s) 1230) in response to training requests.

In some embodiments, the model training system 1220 includes a processing unit, a network interface, a computer-readable medium drive, and an input/output device interface, all of which can communicate with one another by way of a communication bus. The network interface can provide connectivity to one or more networks or computing systems. The processing unit can thus receive information and instructions from other computing systems or services (e.g., user devices 1202, the model hosting system 1240, etc.). The processing unit can also communicate to and from a memory of a virtual machine instance 1222 and further provide output information for an optional display via the input/output device interface. The input/output device interface can also accept input from an optional input device. The memory can contain computer program instructions (grouped as modules in some embodiments) that the processing unit executes in order to implement one or more aspects of the present disclosure.

In some embodiments, the model hosting system 1240 includes a single physical computing device or multiple physical computing devices that are interconnected using one or more computing networks (not shown), where the physical computing device(s) host one or more virtual machine instances 1242. The model hosting system 1240 can handle the acquisition and configuration of compute capacity (e.g., containers, instances, etc.) based on demand for the execution of trained ML models. The model hosting system 1240 can then execute ML models using the compute capacity, as is described in greater detail below. The model hosting system 1240 can automatically scale up and down based on the volume of execution requests received from user devices 1202 via frontend 1249 of the model hosting system 1240, thereby relieving the user from the burden of having to worry about over-utilization (e.g., acquiring too little computing resources and suffering performance issues) or under-utilization (e.g., acquiring more computing resources than necessary to run the ML models, and thus overpaying).

In some embodiments, the virtual machine instances 1242 are utilized to execute tasks. For example, such tasks can include executing an ML model. As shown in FIG. 12, each virtual machine instance 1242 includes an operating system (OS) 1244, a language runtime 1246, and one or more ML scoring containers 1250. The ML scoring containers 1250 are similar to the ML training containers 1230 in that the ML scoring containers 1250 are logical units created within a virtual machine instance using the resources available on that instance and can be utilized to isolate execution of a task from other processes (e.g., task executions) occurring in the instance. In some embodiments, the ML scoring containers 1250 are formed from one or more container images and a top container layer. Each container image further includes one or more image layers, where each image layer represents an executable instruction. As described above, some or all of the executable instructions together represent an algorithm that defines an ML model. Changes made to the ML scoring containers 1250 (e.g., creation of new files, modification of existing files, deletion of files, etc.) are stored in the top container layer. If an ML scoring container 1250 is deleted, the top container layer is also deleted. However, the container image(s) that form a portion of the deleted ML scoring container 1250 can remain unchanged. The ML scoring containers 1250 can be implemented, for example, as Linux containers.

The ML scoring containers 1250 each include a runtime 1254, code 1256, and dependencies 1252 (e.g., supporting software such as libraries) needed by the code 1256 in some embodiments. The runtime 1254 can be defined by one or more executable instructions that form at least a portion of a container image that is used to form the ML scoring container 1250 (e.g., the executable instruction(s) in the container image that define the operating system and/or runtime to run in the container formed from the container image). The code 1256 includes one or more executable instructions that form at least a portion of a container image that is used to form the ML scoring container 1250. For example, the code 1256 includes the executable instructions in the container image that represent an algorithm that defines an ML model, which may reference dependencies 1252. The code 1256 can also include model data that represent characteristics of the defined ML model, as described in greater detail below. The runtime 1254 is configured to execute the code 1256 in response to an instruction to begin execution of an ML model. Execution of the code 1256 results in the generation of outputs (e.g., predicted or "inferred" results), as described in greater detail below.

In some embodiments, the runtime 1254 is the same as the runtime 1246 utilized by the virtual machine instance 1242. In some embodiments, runtime 1254 is different than the runtime 1246 utilized by the virtual machine instance 1242.

In some embodiments, the model hosting system 1240 uses one or more container images included in a deployment request (or a container image retrieved from the container data store 1270 in response to a received deployment request) to create and initialize an ML scoring container 1250 in a virtual machine instance 1242. For example, the model hosting system 1240 creates an ML scoring container 1250 that includes the container image(s) and/or a top container layer.

As described above, a user device 1202 can submit a deployment request and/or an execution request to the model hosting system 1240 via the frontend 1249 in some embodiments. A deployment request causes the model hosting system 1240 to deploy a trained ML model into a virtual machine instance 1242. For example, the deployment request can include an identification of an endpoint (e.g., an endpoint name, such as an HTTP endpoint name) and an identification of one or more trained ML models (e.g., a location of one or more model data files stored in the training model data store 1275). Optionally, the deployment request also includes an identification of one or more container images stored in the container data store 1270.

Upon receiving the deployment request, the model hosting system 1240 initializes ones or more ML scoring containers 1250 in one or more hosted virtual machine instance 1242. In embodiments in which the deployment request includes an identification of one or more container images, the model hosting system 1240 forms the ML scoring container(s) 1250 from the identified container image(s). For example, a container image identified in a deployment request can be the same container image used to form an ML training container 1230 used to train the ML model corresponding to the deployment request. Thus, the code 1256 of the ML scoring container(s) 1250 includes one or more executable instructions in the container image(s) that represent an algorithm that defines an ML model. In embodiments in which the deployment request does not include an identification of a container image, the model hosting system 1240 forms the ML scoring container(s) 1250 from one or more container images stored in the container data store 1270 that are appropriate for executing the identified trained ML model(s). For example, an appropriate container image can be a container image that includes executable instructions that represent an algorithm that defines the identified trained ML model(s).

The model hosting system 1240 further forms the ML scoring container(s) 1250 by retrieving model data corresponding to the identified trained ML model(s) in some embodiments. For example, the deployment request can identify a location of model data file(s) stored in the training model data store 1275. In embodiments in which a single model data file is identified in the deployment request, the model hosting system 1240 retrieves the identified model data file from the training model data store 1275 and inserts the model data file into a single ML scoring container 1250, which forms a portion of code 1256. In some embodiments, the model data file is archived or compressed (e.g., formed from a package of individual files). Thus, the model hosting system 1240 unarchives or decompresses the model data file to obtain multiple individual files and inserts the individual files into the ML scoring container 1250. In some embodiments, the model hosting system 1240 stores the model data file in the same location as the location in which the model data file was stored in the ML training container 1230 that generated the model data file. For example, the model data file initially was stored in the top container layer of the ML training container 1230 at a certain offset, and the model hosting system 1240 then stores the model data file in the top container layer of the ML scoring container 1250 at the same offset.

In embodiments in which multiple model data files are identified in the deployment request, the model hosting system 1240 retrieves the identified model data files from the training model data store 1275. The model hosting system 1240 can insert the model data files into the same ML scoring container 1250, into different ML scoring containers 1250 initialized in the same virtual machine instance 1242, or into different ML scoring containers 1250 initialized in different virtual machine instances 1242. As an illustrative example, the deployment request can identify multiple model data files corresponding to different trained ML models because the trained ML models are related (e.g., the output of one trained ML model is used as an input to another trained ML model). Thus, the user may desire to deploy multiple ML models to eventually receive a single output that relies on the outputs of multiple ML models.

In some embodiments, the model hosting system 1240 associates the initialized ML scoring container(s) 1250 with the endpoint identified in the deployment request. For example, each of the initialized ML scoring container(s) 1250 can be associated with a network address. The model hosting system 1240 can map the network address(es) to the identified endpoint, and the model hosting system 1240 or another system (e.g., a routing system, not shown) can store the mapping. Thus, a user device 1202 can refer to trained ML model(s) stored in the ML scoring container(s) 1250 using the endpoint. This allows for the network address of an ML scoring container 1250 to change without causing the user operating the user device 1202 to change the way in which the user refers to a trained ML model.

Once the ML scoring container(s) 1250 are initialized, the ML scoring container(s) 1250 are ready to execute trained ML model(s). In some embodiments, the user device 1202 transmits an execution request to the model hosting system 1240 via the frontend 1249, where the execution request identifies an endpoint and includes an input to an ML model (e.g., a set of input data). The model hosting system 1240 or another system (e.g., a routing system, not shown) can obtain the execution request, identify the ML scoring container(s) 1250 corresponding to the identified endpoint, and route the input to the identified ML scoring container(s) 1250.

In some embodiments, a virtual machine instance 1242 executes the code 1256 stored in an identified ML scoring container 1250 in response to the model hosting system 1240 receiving the execution request. In particular, execution of the code 1256 causes the executable instructions in the code 1256 corresponding to the algorithm to read the model data file stored in the ML scoring container 1250, use the input included in the execution request as an input parameter, and generate a corresponding output. As an illustrative example, the algorithm can include coefficients, weights, layers, cluster centroids, and/or the like. The executable instructions in the code 1256 corresponding to the algorithm can read the model data file to determine values for the coefficients, weights, layers, cluster centroids, and/or the like. The executable instructions can include input parameters, and the input included in the execution request can be supplied by the virtual machine instance 1242 as the input parameters. With the ML model characteristics and the input parameters provided, execution of the executable instructions by the virtual machine instance 1242 can be completed, resulting in an output.

In some embodiments, the virtual machine instance 1242 stores the output in the model prediction data store 1280. Alternatively or in addition, the virtual machine instance 1242 transmits the output to the user device 1202 that submitted the execution result via the frontend 1249.

In some embodiments, the execution request corresponds to a group of related trained ML models. Thus, the ML scoring container 1250 can transmit the output to a second ML scoring container 1250 initialized in the same virtual machine instance 1242 or in a different virtual machine instance 1242. The virtual machine instance 1242 that initialized the second ML scoring container 1250 can then execute second code 1256 stored in the second ML scoring container 1250, providing the received output as an input parameter to the executable instructions in the second code 1256. The second ML scoring container 1250 further includes a model data file stored therein, which is read by the executable instructions in the second code 1256 to determine values for the characteristics defining the ML model. Execution of the second code 1256 results in a second output. The virtual machine instance 1242 that initialized the second ML scoring container 1250 can then transmit the second output to the model prediction data store 1280 and/or the user device 1202 via the frontend 1249 (e.g., if no more trained ML models are needed to generate an output) or transmit the second output to a third ML scoring container 1250 initialized in the same or different virtual machine instance 1242 (e.g., if outputs from one or more additional trained ML models are needed), and the above-referenced process can be repeated with respect to the third ML scoring container 1250.

While the virtual machine instances 1242 are shown in FIG. 12 as a single grouping of virtual machine instances 1242, some embodiments of the present application separate virtual machine instances 1242 that are actively assigned to execute tasks from those virtual machine instances 1242 that are not actively assigned to execute tasks. For example, those virtual machine instances 1242 actively assigned to execute tasks are grouped into an "active pool," while those virtual machine instances 1242 not actively assigned to execute tasks are placed within a "warming pool." In some embodiments, those virtual machine instances 1242 within the warming pool can be pre-initialized with an operating system, language runtimes, and/or other software required to enable rapid execution of tasks (e.g., rapid initialization of ML scoring container(s) 1250, rapid execution of code 1256 in ML scoring container(s), etc.) in response to deployment and/or execution requests.

In some embodiments, the model hosting system 1240 includes a processing unit, a network interface, a computer-readable medium drive, and an input/output device interface, all of which can communicate with one another by way of a communication bus. The network interface can provide connectivity to one or more networks or computing systems. The processing unit can thus receive information and instructions from other computing systems or services (e.g., user devices 1202, the model training system 1220, etc.). The processing unit can also communicate to and from a memory of a virtual machine instance 1242 and further provide output information for an optional display via the input/output device interface. The input/output device interface can also accept input from an optional input device. The memory can contain computer program instructions (grouped as modules in some embodiments) that the processing unit executes in order to implement one or more aspects of the present disclosure.

In some embodiments, the operating environment supports many different types of ML models, such as multi-arm bandit models, reinforcement learning models, ensemble ML models, deep learning models, or the like.

The model training system 1220 and the model hosting system 1240 depicted in FIG. 12 are not meant to be limiting. For example, the model training system 1220 and/or the model hosting system 1240 could also operate within a computing environment having a fewer or greater number of devices than are illustrated in FIG. 12. Thus, the depiction of the model training system 1220 and/or the model hosting system 1240 in FIG. 12 may be taken as illustrative and not limiting to the present disclosure. For example, the model training system 1220 and/or the model hosting system 1240 or various constituents thereof could implement various Web services components, hosted or "cloud" computing environments, and/or peer-to-peer network configurations to implement at least a portion of the processes described herein. In some embodiments, the model training system 1220 and/or the model hosting system 1240 are implemented directly in hardware or software executed by hardware devices and may, for instance, include one or more physical or virtual servers implemented on physical computer hardware configured to execute computer-executable instructions for performing the various features that are described herein. The one or more servers can be geographically dispersed or geographically co-located, for instance, in one or more points of presence (POPs) or regional data centers.

The frontend 1229 processes all training requests received from user devices 1202 and provisions virtual machine instances 1222. In some embodiments, the frontend 1229 serves as a front door to all the other services provided by the model training system 1220. The frontend 1229 processes the requests and makes sure that the requests are properly authorized. For example, the frontend 1229 may determine whether the user associated with the training request is authorized to initiate the training process.

Similarly, frontend 1249 processes all deployment and execution requests received from user devices 1202 and provisions virtual machine instances 1242. In some embodiments, the frontend 1249 serves as a front door to all the other services provided by the model hosting system 1240. The frontend 1249 processes the requests and makes sure that the requests are properly authorized. For example, the frontend 1249 may determine whether the user associated with a deployment request or an execution request is authorized to access the indicated model data and/or to execute the indicated ML model.

The training data store 1260 stores training data and/or evaluation data. The training data can be data used to train ML models and evaluation data can be data used to evaluate the performance of ML models. In some embodiments, the training data and the evaluation data have common data. In some embodiments, the training data and the evaluation data do not have common data. In some embodiments, the training data includes input data and expected outputs. While the training data store 1260 is depicted as being located external to the model training system 1220 and the model hosting system 1240, this is not meant to be limiting. For example, in some embodiments not shown, the training data store 1260 is located internal to at least one of the model training system 1220 or the model hosting system 1240.

In some embodiments, the training metrics data store 1265 stores model metrics. While the training metrics data store 1265 is depicted as being located external to the model training system 1220 and the model hosting system 1240, this is not meant to be limiting. For example, in some embodiments not shown, the training metrics data store 1265 is located internal to at least one of the model training system 1220 or the model hosting system 1240.

The container data store 1270 stores container images, such as container images used to form ML training containers 1230 and/or ML scoring containers 1250, that can be retrieved by various virtual machine instances 1222 and/or 1242. While the container data store 1270 is depicted as being located external to the model training system 1220 and the model hosting system 1240, this is not meant to be limiting. For example, in some embodiments not shown, the container data store 1270 is located internal to at least one of the model training system 1220 and the model hosting system 1240.

The training model data store 1275 stores model data files. In some embodiments, some of the model data files are comprised of a single file, while other model data files are packages of multiple individual files. While the training model data store 1275 is depicted as being located external to the model training system 1220 and the model hosting system 1240, this is not meant to be limiting. For example, in some embodiments not shown, the training model data store 1275 is located internal to at least one of the model training system 1220 or the model hosting system 1240.

The model prediction data store 1280 stores outputs (e.g., execution results) generated by the ML scoring containers 1250 in some embodiments. While the model prediction data store 1280 is depicted as being located external to the model training system 1220 and the model hosting system 1240, this is not meant to be limiting. For example, in some embodiments not shown, the model prediction data store 1280 is located internal to at least one of the model training system 1220 and the model hosting system 1240.

While the model training system 1220, the model hosting system 1240, the training data store 1260, the training metrics data store 1265, the container data store 1270, the training model data store 1275, and the model prediction data store 1280 are illustrated as separate components, this is not meant to be limiting. In some embodiments, any one or all of these components can be combined to perform the functionality described herein. For example, any one or all of these components can be implemented by a single computing device, or by multiple distinct computing devices, such as computer servers, logically or physically grouped together to collectively operate as a server system. Any one or all of these components can communicate via a shared internal network, and the collective system (e.g., also referred to herein as an ML service) can communicate with one or more of the user devices 1202 via the one or more network(s) 106.

Various example user devices 1202 are shown in FIG. 12, including a desktop computer, laptop, and a mobile phone, each provided by way of illustration. In general, the user devices 1202 can be any computing device such as a desktop, laptop or tablet computer, personal computer, wearable computer, server, personal digital assistant (PDA), hybrid PDA/mobile phone, mobile phone, electronic book reader, set-top box, voice command device, camera, digital media player, and the like. In some embodiments, the model training system 1220 and/or the model hosting system 1240 provides the user devices 1202 with one or more user interfaces, command-line interfaces (CLI), application programing interfaces (API), and/or other programmatic interfaces for submitting training requests, deployment requests, and/or execution requests. In some embodiments, the user devices 1202 can execute a stand-alone application that interacts with the model training system 1220 and/or the model hosting system 1240 for submitting training requests, deployment requests, and/or execution requests.

In some embodiments, the network 106 includes any wired network, wireless network, or combination thereof. For example, the network 106 may be a personal area network, local area network, wide area network, over-the-air broadcast network (e.g., for radio or television), cable network, satellite network, cellular telephone network, or combination thereof. As a further example, the network 106 may be a publicly accessible network of linked networks, possibly operated by various distinct parties, such as the Internet. In some embodiments, the network 106 may be a private or semi-private network, such as a corporate or university intranet. The network 106 may include one or more wireless networks, such as a Global System for Mobile Communications (GSM) network, a Code Division Multiple Access (CDMA) network, a Long Term Evolution (LTE) network, or any other type of wireless network. The network 106 can use protocols and components for communicating via the Internet or any of the other aforementioned types of networks. For example, the protocols used by the network 106 may include HTTP, HTTP Secure (HTTPS), Message Queue Telemetry Transport (MQTT), Constrained Application Protocol (CoAP), and the like. Protocols and components for communicating via the Internet or any of the other aforementioned types of communication networks are well known to those skilled in the art and, thus, are not described in more detail herein.

Figure 13:
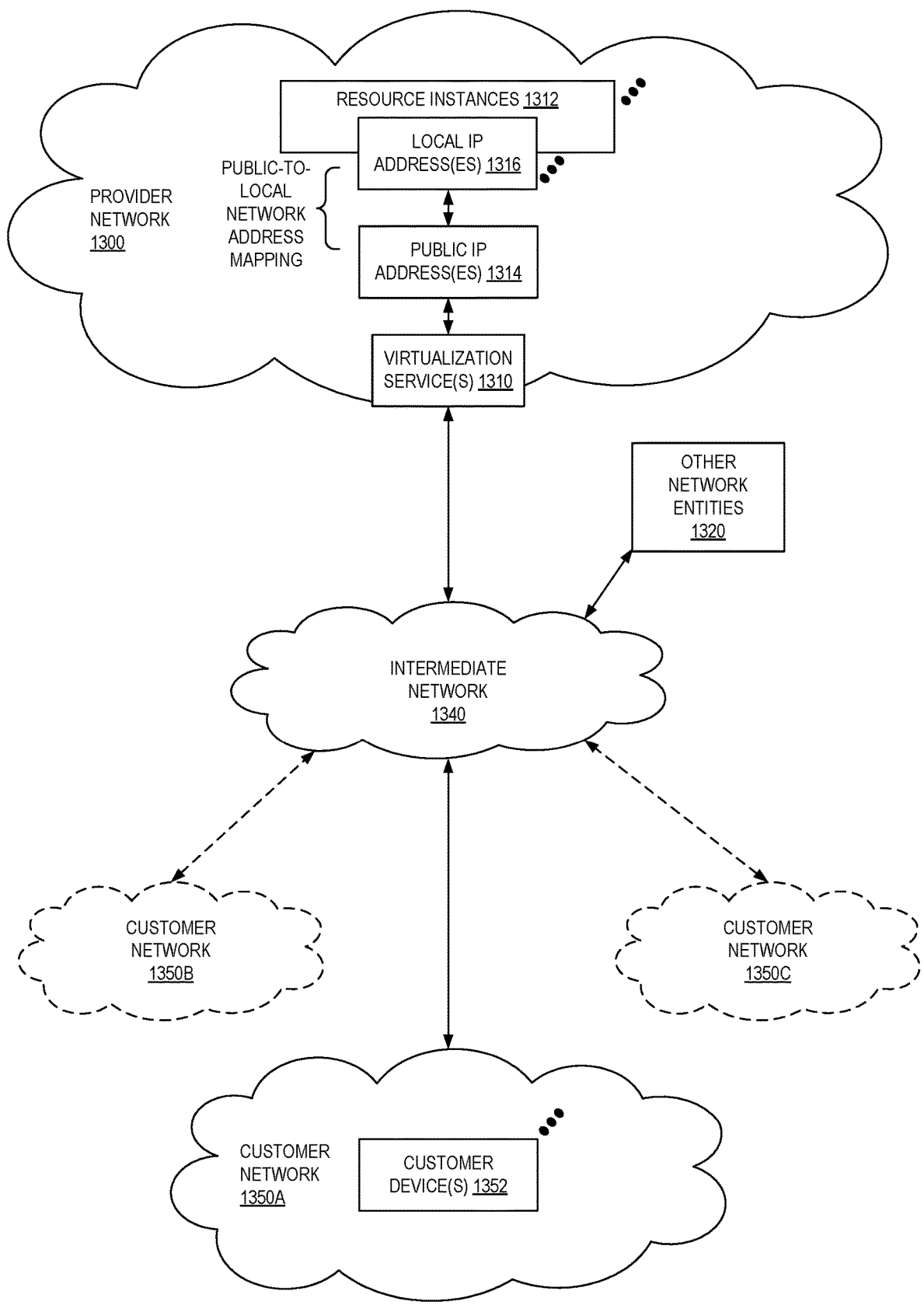
FIG. 13 illustrates an example provider network environment according to some embodiments.

FIG. 13 illustrates an example provider network (or "service provider system") environment according to some embodiments. A provider network 1300 may provide resource virtualization to customers via one or more virtualization services 1310 that allow customers to purchase, rent, or otherwise obtain instances 1312 of virtualized resources, including but not limited to computation and storage resources, implemented on devices within the provider network or networks in one or more data centers. Local Internet Protocol (IP) addresses 1316 may be associated with the resource instances 1312; the local IP addresses are the internal network addresses of the resource instances 1312 on the provider network 1300. In some embodiments, the provider network 1300 may also provide public IP addresses 1314 and/or public IP address ranges (e.g., Internet Protocol version 4 (IPv4) or Internet Protocol version 6 (IPv6) addresses) that customers may obtain from the provider 1300.

Conventionally, the provider network 1300, via the virtualization services 1310, may allow a customer of the service provider (e.g., a customer that operates one or more client networks 1350A-1350C including one or more customer device(s) 1352) to dynamically associate at least some public IP addresses 1314 assigned or allocated to the customer with particular resource instances 1312 assigned to the customer. The provider network 1300 may also allow the customer to remap a public IP address 1314, previously mapped to one virtualized computing resource instance 1312 allocated to the customer, to another virtualized computing resource instance 1312 that is also allocated to the customer. Using the virtualized computing resource instances 1312 and public IP addresses 1314 provided by the service provider, a customer of the service provider such as the operator of customer network(s) 1350A-1350C may, for example, implement customer-specific applications and present the customer's applications on an intermediate network 1340, such as the Internet. Other network entities 1320 on the intermediate network 1340 may then generate traffic to a destination public IP address 1314 published by the customer network(s) 1350A-1350C; the traffic is routed to the service provider data center, and at the data center is routed, via a network substrate, to the local IP address 1316 of the virtualized computing resource instance 1312 currently mapped to the destination public IP address 1314. Similarly, response traffic from the virtualized computing resource instance 1312 may be routed via the network substrate back onto the intermediate network 1340 to the source entity 1320.

Local IP addresses, as used herein, refer to the internal or "private" network addresses, for example, of resource instances in a provider network. Local IP addresses can be within address blocks reserved by Internet Engineering Task Force (IETF) Request for Comments (RFC) 1918 and/or of an address format specified by IETF RFC 4193 and may be mutable within the provider network. Network traffic originating outside the provider network is not directly routed to local IP addresses; instead, the traffic uses public IP addresses that are mapped to the local IP addresses of the resource instances. The provider network may include networking devices or appliances that provide network address translation (NAT) or similar functionality to perform the mapping from public IP addresses to local IP addresses and vice versa.

Public IP addresses are Internet mutable network addresses that are assigned to resource instances, either by the service provider or by the customer. Traffic routed to a public IP address is translated, for example via 1:1 NAT, and forwarded to the respective local IP address of a resource instance.

Some public IP addresses may be assigned by the provider network infrastructure to particular resource instances; these public IP addresses may be referred to as standard public IP addresses, or simply standard IP addresses. In some embodiments, the mapping of a standard IP address to a local IP address of a resource instance is the default launch configuration for all resource instance types.

At least some public IP addresses may be allocated to or obtained by customers of the provider network 1300; a customer may then assign their allocated public IP addresses to particular resource instances allocated to the customer. These public IP addresses may be referred to as customer public IP addresses, or simply customer IP addresses. Instead of being assigned by the provider network 1300 to resource instances as in the case of standard IP addresses, customer IP addresses may be assigned to resource instances by the customers, for example via an API provided by the service provider. Unlike standard IP addresses, customer IP addresses are allocated to customer accounts and can be remapped to other resource instances by the respective customers as necessary or desired. A customer IP address is associated with a customer's account, not a particular resource instance, and the customer controls that IP address until the customer chooses to release it. Unlike conventional static IP addresses, customer IP addresses allow the customer to mask resource instance or availability zone failures by remapping the customer's public IP addresses to any resource instance associated with the customer's account. The customer IP addresses, for example, enable a customer to engineer around problems with the customer's resource instances or software by remapping customer IP addresses to replacement resource instances.

Figure 14:
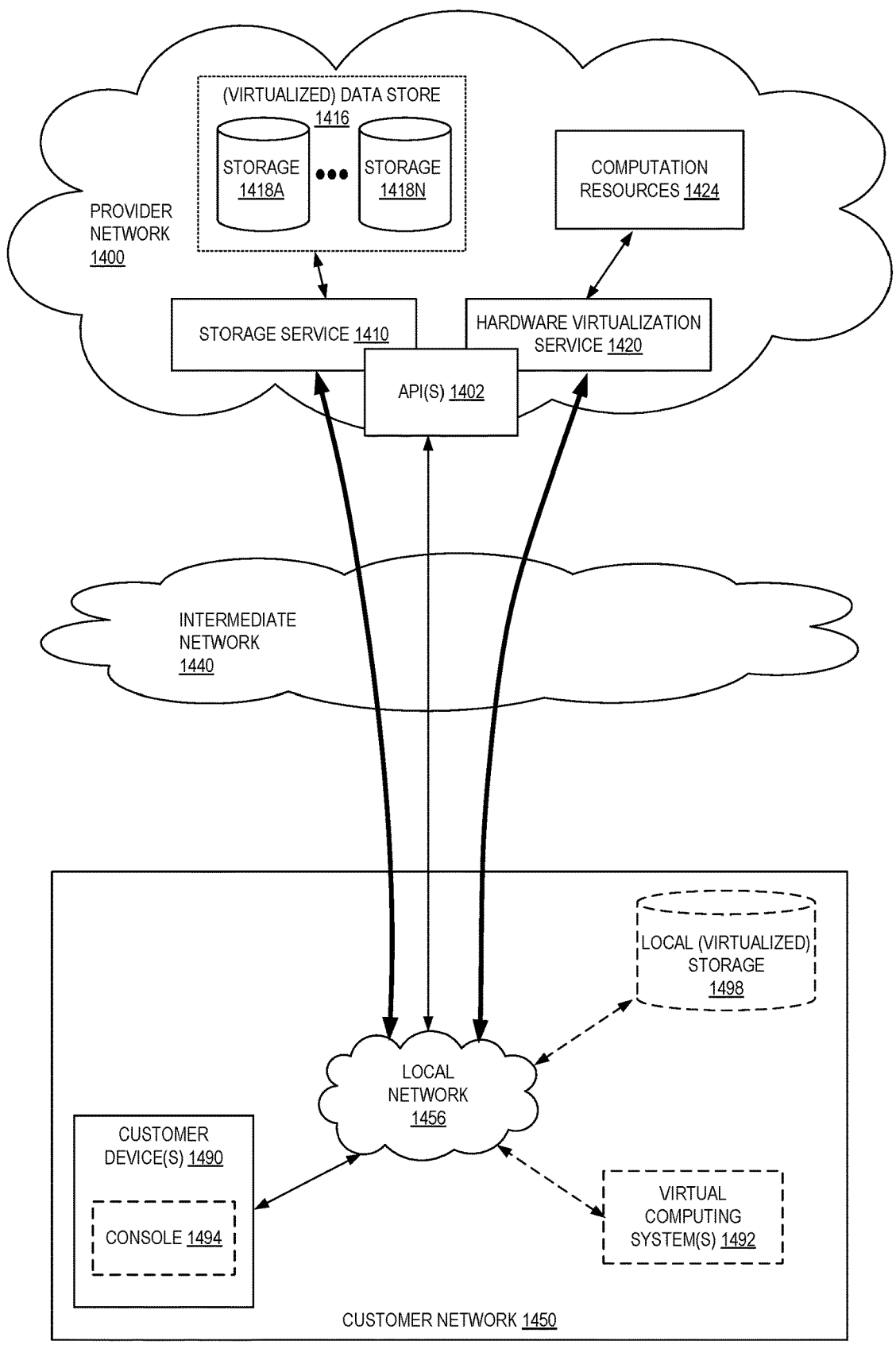
FIG. 14 is a block diagram of an example provider network that provides a storage service and a hardware virtualization service to customers according to some embodiments.

FIG. 14 is a block diagram of an example provider network that provides a storage service and a hardware virtualization service to customers, according to some embodiments. Hardware virtualization service 1420 provides multiple computation resources 1424 (e.g., VMs) to customers. The computation resources 1424 may, for example, be rented or leased to customers of the provider network 1400 (e.g., to a customer that implements customer network 1450). Each computation resource 1424 may be provided with one or more local IP addresses. Provider network 1400 may be configured to route packets from the local IP addresses of the computation resources 1424 to public Internet destinations, and from public Internet sources to the local IP addresses of computation resources 1424.

Provider network 1400 may provide a customer network 1450, for example coupled to intermediate network 1440 via local network 1456, the ability to implement virtual computing systems 1492 via hardware virtualization service 1420 coupled to intermediate network 1440 and to provider network 1400. In some embodiments, hardware virtualization service 1420 may provide one or more APIs 1402, for example a web services interface, via which a customer network 1450 may access functionality provided by the hardware virtualization service 1420, for example via a console 1494 (e.g., a web-based application, standalone application, mobile application, etc.). In some embodiments, at the provider network 1400, each virtual computing system 1492 at customer network 1450 may correspond to a computation resource 1424 that is leased, rented, or otherwise provided to customer network 1450.

From an instance of a virtual computing system 1492 and/or another customer device 1490 (e.g., via console 1494), the customer may access the functionality of storage service 1410, for example via one or more APIs 1402, to access data from and store data to storage resources 1418A-1418N of a virtual data store 1416 (e.g., a folder or "bucket", a virtualized volume, a database, etc.) provided by the provider network 1400. In some embodiments, a virtualized data store gateway (not shown) may be provided at the customer network 1450 that may locally cache at least some data, for example frequently-accessed or critical data, and that may communicate with storage service 1410 via one or more communications channels to upload new or modified data from a local cache so that the primary store of data (virtualized data store 1416) is maintained. In some embodiments, a user, via a virtual computing system 1492 and/or on another customer device 1490, may mount and access virtual data store 1416 volumes via storage service 1410 acting as a storage virtualization service, and these volumes may appear to the user as local (virtualized) storage 1498.

While not shown in FIG. 14, the virtualization service(s) may also be accessed from resource instances within the provider network 1400 via API(s) 1402. For example, a customer, appliance service provider, or other entity may access a virtualization service from within a respective virtual network on the provider network 1400 via an API 1402 to request allocation of one or more resource instances within the virtual network or within another virtual network.

Illustrative Systems

Figure 15:
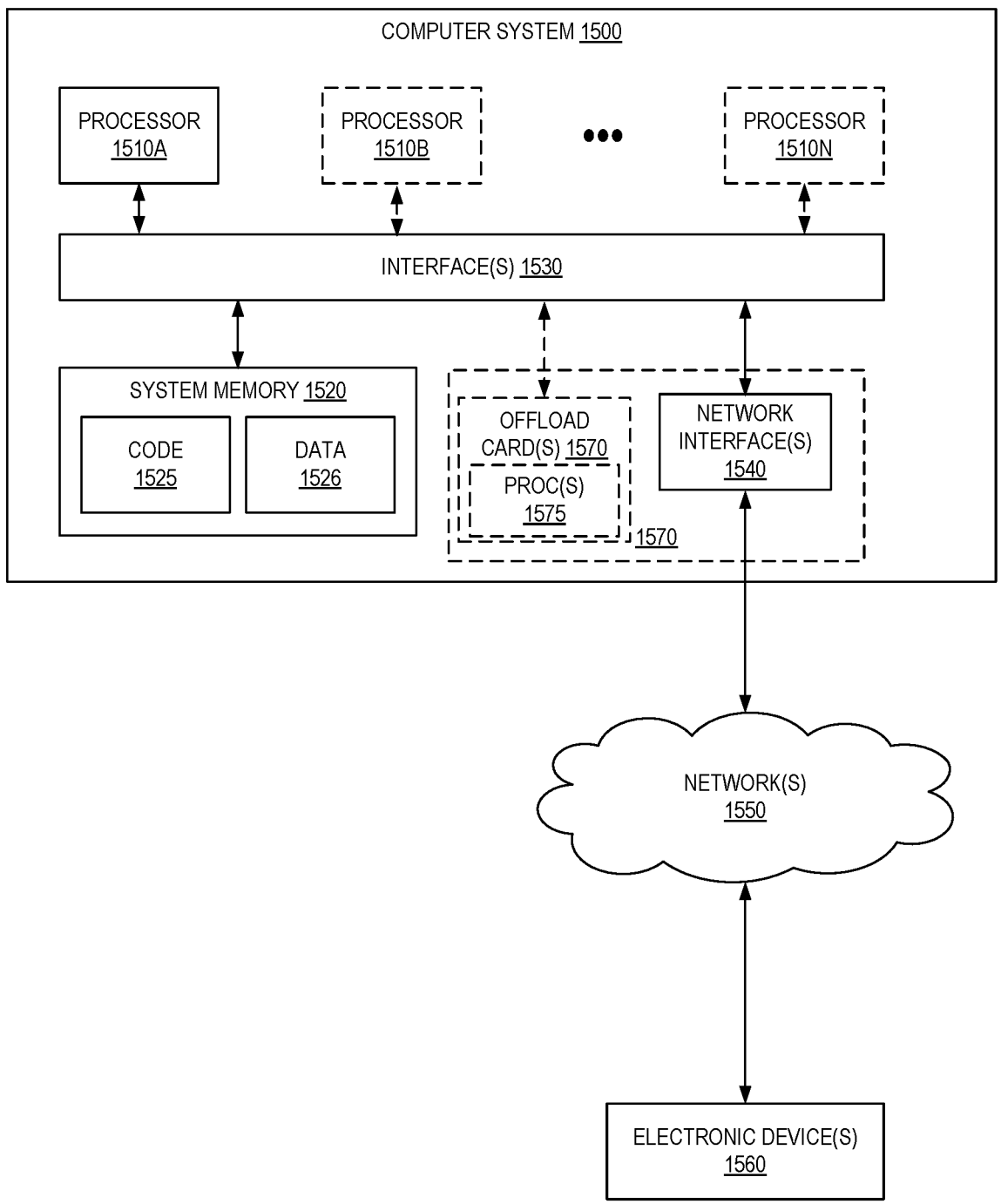
FIG. 15 is a block diagram illustrating an example computer system that may be used in some embodiments.

In some embodiments, a system that implements a portion or all of the techniques described herein may include a general-purpose computer system that includes or is configured to access one or more computer-accessible media, such as computer system 1500 illustrated in FIG. 15. In the illustrated embodiment, computer system 1500 includes one or more processors 1510 coupled to a system memory 1520 via an input/output (I/O) interface 1530. Computer system 1500 further includes a network interface 1540 coupled to I/O interface 1530. While FIG. 15 shows computer system 1500 as a single computing device, in various embodiments a computer system 1500 may include one computing device or any number of computing devices configured to work together as a single computer system 1500.

In various embodiments, computer system 1500 may be a uniprocessor system including one processor 1510, or a multiprocessor system including several processors 1510 (e.g., two, four, eight, or another suitable number). Processors 1510 may be any suitable processors capable of executing instructions. For example, in various embodiments, processors 1510 may be general-purpose or embedded processors implementing any of a variety of instruction set architectures (ISAs), such as the x86, ARM, PowerPC, SPARC, or MIPS ISAs, or any other suitable ISA. In multiprocessor systems, each of processors 1510 may commonly, but not necessarily, implement the same ISA.

System memory 1520 may store instructions and data accessible by processor(s) 1510. In various embodiments, system memory 1520 may be implemented using any suitable memory technology, such as random-access memory (RAM), static RAM (SRAM), synchronous dynamic RAM (SDRAM), nonvolatile/Flash-type memory, or any other type of memory. In the illustrated embodiment, program instructions and data implementing one or more desired functions, such as those methods, techniques, and data described above are shown stored within system memory 1520 as code 1525 and data 1526.

In one embodiment, I/O interface 1530 may be configured to coordinate I/O traffic between processor 1510, system memory 1520, and any peripheral devices in the device, including network interface 1540 or other peripheral interfaces. In some embodiments, I/O interface 1530 may perform any necessary protocol, timing or other data transformations to convert data signals from one component (e.g., system memory 1520) into a format suitable for use by another component (e.g., processor 1510). In some embodiments, I/O interface 1530 may include support for devices attached through various types of peripheral buses, such as a variant of the Peripheral Component Interconnect (PCI) bus standard or the Universal Serial Bus (USB) standard, for example. In some embodiments, the function of I/O interface 1530 may be split into two or more separate components, such as a north bridge and a south bridge, for example. Also, in some embodiments some or all of the functionality of I/O interface 1530, such as an interface to system memory 1520, may be incorporated directly into processor 1510.

Network interface 1540 may be configured to allow data to be exchanged between computer system 1500 and other devices 1560 attached to a network or networks 1550, such as other computer systems or devices as illustrated in FIG. 1, for example. In various embodiments, network interface 1540 may support communication via any suitable wired or wireless general data networks, such as types of Ethernet network, for example. Additionally, network interface 1540 may support communication via telecommunications/telephony networks such as analog voice networks or digital fiber communications networks, via storage area networks (SANs) such as Fibre Channel SANs, or via I/O any other suitable type of network and/or protocol.

In some embodiments, a computer system 1500 includes one or more offload cards 1570 (including one or more processors 1575, and possibly including the one or more network interfaces 1540) that are connected using an I/O interface 1530 (e.g., a bus implementing a version of the Peripheral Component Interconnect-Express (PCI-E) standard, or another interconnect such as a QuickPath interconnect (QPI) or UltraPath interconnect (UPI)). For example, in some embodiments the computer system 1500 may act as a host electronic device (e.g., operating as part of a hardware virtualization service) that hosts compute instances, and the one or more offload cards 1570 execute a virtualization manager that can manage compute instances that execute on the host electronic device. As an example, in some embodiments the offload card(s) 1570 can perform compute instance management operations such as pausing and/or un-pausing compute instances, launching and/or terminating compute instances, performing memory transfer/copying operations, etc. These management operations may, in some embodiments, be performed by the offload card(s) 1570 in coordination with a hypervisor (e.g., upon a request from a hypervisor) that is executed by the other processors 1510A-1510N of the computer system 1500. However, in some embodiments the virtualization manager implemented by the offload card(s) 1570 can accommodate requests from other entities (e.g., from compute instances themselves), and may not coordinate with (or service) any separate hypervisor.

In some embodiments, system memory 1520 may be one embodiment of a computer-accessible medium configured to store program instructions and data as described above. However, in other embodiments, program instructions and/or data may be received, sent or stored upon different types of computer-accessible media. Generally speaking, a computer-accessible medium may include non-transitory storage media or memory media such as magnetic or optical media, e.g., disk or DVD/CD coupled to computer system 1500 via I/O interface 1530. A non-transitory computer-accessible storage medium may also include any volatile or non-volatile media such as RAM (e.g., SDRAM, double data rate (DDR) SDRAM, SRAM, etc.), read only memory (ROM), etc., that may be included in some embodiments of computer system 1500 as system memory 1520 or another type of memory. Further, a computer-accessible medium may include transmission media or signals such as electrical, electromagnetic, or digital signals, conveyed via a communication medium such as a network and/or a wireless link, such as may be implemented via network interface 1540.

Various embodiments discussed or suggested herein can be implemented in a wide variety of operating environments, which in some cases can include one or more user computers, computing devices, or processing devices which can be used to operate any of a number of applications. User or client devices can include any of a number of general-purpose personal computers, such as desktop or laptop computers running a standard operating system, as well as cellular, wireless, and handheld devices running mobile software and capable of supporting a number of networking and messaging protocols. Such a system also can include a number of workstations running any of a variety of commercially available operating systems and other known applications for purposes such as development and database management. These devices also can include other electronic devices, such as dummy terminals, thin-clients, gaming systems, and/or other devices capable of communicating via a network.

Most embodiments utilize at least one network that would be familiar to those skilled in the art for supporting communications using any of a variety of widely-available protocols, such as Transmission Control Protocol/Internet Protocol (TCP/IP), File Transfer Protocol (FTP), Universal Plug and Play (UPnP), Network File System (NFS), Common Internet File System (CIFS), Extensible Messaging and Presence Protocol (XMPP), AppleTalk, etc. The network(s) can include, for example, a local area network (LAN), a wide-area network (WAN), a virtual private network (VPN), the Internet, an intranet, an extranet, a public switched telephone network (PSTN), an infrared network, a wireless network, and any combination thereof.

In embodiments utilizing a web server, the web server can run any of a variety of server or mid-tier applications, including HTTP servers, File Transfer Protocol (FTP) servers, Common Gateway Interface (CGI) servers, data servers, Java servers, business application servers, etc. The server(s) also may be capable of executing programs or scripts in response requests from user devices, such as by executing one or more Web applications that may be implemented as one or more scripts or programs written in any programming language, such as Java®, C, C# or C++, or any scripting language, such as Perl, Python, PHP, or TCL, as well as combinations thereof. The server(s) may also include database servers, including without limitation those commercially available from Oracle®, Microsoft®, Sybase®, IBM®, etc. The database servers may be relational or non-relational (e.g., "NoSQL"), distributed or non-distributed, etc.

Environments disclosed herein can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and/or at least one output device (e.g., a display device, printer, or speaker). Such a system may also include one or more storage devices, such as disk drives, optical storage devices, and solid-state storage devices such as random-access memory (RAM) or read-only memory (ROM), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or web browser. It should be appreciated that alternate embodiments may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, Electrically Erasable Programmable Read-Only Memory (EEPROM), flash memory or other memory technology, Compact Disc-Read Only Memory (CD-ROM), Digital Versatile Disk (DVD) or other optical storage, magnetic cassettes, magnetic tape, magnetic disk storage or other magnetic storage devices, or any other medium which can be used to store the desired information and which can be accessed by a system device. Based on the disclosure and teachings provided herein, a person of ordinary skill in the art will appreciate other ways and/or methods to implement the various embodiments.

In the preceding description, various embodiments are described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Bracketed text and blocks with dashed borders (e.g., large dashes, small dashes, dot-dash, and dots) are used herein to illustrate optional operations that add additional features to some embodiments. However, such notation should not be taken to mean that these are the only options or optional operations, and/or that blocks with solid borders are not optional in certain embodiments.

Reference numerals with suffix letters (e.g., 1418A-1418N) may be used to indicate that there can be one or multiple instances of the referenced entity in various embodiments, and when there are multiple instances, each does not need to be identical but may instead share some general traits or act in common ways. Further, the particular suffixes used are not meant to imply that a particular amount of the entity exists unless specifically indicated to the contrary. Thus, two entities using the same or different suffix letters may or may not have the same number of instances in various embodiments.

References to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Moreover, in the various embodiments described above, unless specifically noted otherwise, disjunctive language such as the phrase "at least one of A, B, or C" is intended to be understood to mean either A, B, or C, or any combination thereof (e.g., A, B, and/or C). As such, disjunctive language is not intended to, nor should it be understood to, imply that a given embodiment requires at least one of A, at least one of B, or at least one of C to each be present.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

What is claimed is:

1. A computer-implemented method comprising:
receiving, at a web service endpoint of a provider network, a request to link unstructured text to a standardized ontology, the request being originated by a client and including the unstructured text;
identifying a plurality of segments within the unstructured text;
identifying detected entities within the plurality of segments with an entity identification service within the provider network that utilizes a machine learning model trained to detect entities of a particular entity type within the plurality of segments, wherein the particular entity type comprises a medical condition type and an anatomy type, and the entity identification service utilizes a first machine learning model trained to detect entities of the medical condition type and a second machine learning model trained to detect entities of the anatomy type;
identifying one or more relationships between the detected entities with a relationship identification service within the provider network that utilizes a machine learning model trained to detect relationships between entities;
identifying a set of similar candidates of the standardized ontology from the detected entities and the one or more relationships with an ontology search service within the provider network;
ranking the set of similar candidates from the standardized ontology according to their similarity to the detected entities within the unstructured text with a ranking service within the provider network that utilizes a machine learning model trained to rank candidates according to their similarity to entities;
generating a result based at least in part on the ranking, the result identifying at least one highest ranked candidate of the set of similar candidates from the standardized ontology for the detected entities within the unstructured text; and
sending a response including the result to the client.

2. The computer-implemented method of claim 1, wherein the particular entity type comprises a medication type.

3. The computer-implemented method of claim 1, wherein the anatomy type comprises an anatomical body part or system type, and the second machine learning model is trained to detect entities of the anatomical body part or system type.

4. A computer-implemented method comprising:
receiving a request to link unstructured text to a standardized ontology;
executing at least one first machine learning model, trained to detect entities of a particular entity type, on the unstructured text to identify detected entities, wherein the particular entity type comprises a medical condition type and an anatomy type, and the at least one first machine learning model comprises a first entity identification machine learning model trained to detect entities of the medical condition type, and a second entity identification machine learning model trained to detect entities of the anatomy type;

executing a second machine learning model, trained to detect relationships between entities, on the detected entities to identify one or more relationships between the detected entities;

performing a search of the standardized ontology to identify a set of similar candidates from the standardized ontology for the detected entities and the one or more relationships;

executing a third machine learning model, trained to rank candidates according to their similarity to entities, to generate a ranking of the set of similar candidates from the standardized ontology according to their similarity to the detected entities within the unstructured text;

generating a result based at least in part on the ranking, the result identifying at least one candidate of the set of similar candidates from the standardized ontology for the detected entities within the unstructured text; and transmitting the result.

5. The computer-implemented method of claim 4, wherein the particular entity type comprises a medication type, and the at least one first machine learning model comprises an entity identification machine learning model trained to detect entities of the medication type.

6. The computer-implemented method of claim 5, wherein the result is a standardized medication name for medication text in the unstructured text.

7. The computer-implemented method of claim 5, wherein the standardized ontology is a standardized medical ontology for generic and branded medication names.

8. The computer-implemented method of claim 7, wherein the standardized medical ontology for generic and branded medication names comprises an RxNorm data set.

9. The computer-implemented method of claim 4, wherein the anatomy type comprises an anatomical body part or system type, and the second entity identification machine learning model is trained to detect entities of the anatomical body part or system type.

10. The computer-implemented method of claim 4, wherein the result is a standardized medical classification code for medical condition text and anatomical body part or system text in the unstructured text.

11. The computer-implemented method of claim 4, wherein the standardized ontology is a standardized medical ontology for medical classification codes.

12. The computer-implemented method of claim 11, wherein the standardized medical ontology for medical classification codes comprises an International Classification of Diseases (ICD) coding scheme data set.

13. The computer-implemented method of claim 4, wherein each of the machine learning models is executed by a separate virtual machine or container within a provider network.

14. The computer-implemented method of claim 4, further comprising identifying a plurality of segments within the unstructured text, wherein the executing the at least one first machine learning model, executing the second machine learning model, performing the search, and executing the third machine learning model are performed for each segment of the plurality of segments.

15. A system comprising:

a plurality of unstructured text services implemented by a first one or more electronic devices, the plurality of unstructured text services comprising at least one first machine learning model trained to detect entities of a particular entity type, a second machine learning model trained to detect relationships between entities, and a third machine learning model trained to rank candidates according to their similarity to entities; and an orchestrator implemented by a second one or more electronic devices, the orchestrator including instructions that upon execution, for a request to link unstructured text to a standardized ontology, cause:

execution of the at least one first machine learning model, trained to detect entities of the particular entity type, on the unstructured text to identify detected entities, wherein the particular entity type comprises a medical condition type and an anatomy type, and the at least one first machine learning model comprises a first entity identification machine learning model trained to detect entities of the medical condition type, and a second entity identification machine learning model trained to detect entities of the anatomy type, execution of the second machine learning model, trained to detect relationships between entities, on the detected entities to identify one or more relationships between the detected entities, performance of a search of the standardized ontology to identify a set of similar candidates from the standardized ontology for the detected entities and the one or more relationships, execution of the third machine learning model, trained to rank candidates according to their similarity to entities, to generate a ranking of the set of similar candidates from the standardized ontology according to their similarity to the detected entities within the unstructured text, generation of a result based at least in part on the ranking, the result identifying at least one candidate of the set of similar candidates from the standardized ontology for the detected entities within the unstructured text, and transmittal of the result.

16. The system of claim 15, wherein the particular entity type comprises a medication type, and the at least one first machine learning model comprises an entity identification machine learning model trained to detect entities of the medication type.

17. The system of claim 16, wherein the result is a standardized medication name for medication text in the unstructured text.

18. The system of claim 16, wherein the standardized ontology is a standardized medical ontology for generic and branded medication names.

19. The system of claim 15, wherein the anatomy type comprises an anatomical body part or system type, and the second entity identification machine learning model is trained to detect entities of the anatomical body part or system type.

20. The system of claim 15, wherein the result is a standardized medical classification code for medical condition text and anatomical body part or system text in the unstructured text.

* * * * *